(12) United States Patent
Feldhahn et al.

(10) Patent No.: US 7,909,032 B2
(45) Date of Patent: Mar. 22, 2011

(54) VENTILATION DEVICE

(75) Inventors: Karl Andreas Feldhahn, Hamburg (DE); Wolfgang Wedler, Hamburg (DE); Matthias Pulla, Hamburg (DE); Christof Göbel, Hamburg (DE); Thomas Ress, Barmstedt (DE); Frank Herrmann, Barmstedt (DE); Stefan Hein, Hamburg (DE); Christian Kluin, Hamburg (DE); Joachim Gardein, Tenerife, Canary Islands (ES)

(73) Assignee: Weinmann Gerate fur Medizin GmbH & Co. KG, Hamburg (DE)

( * ) Notice: Subject to any disclaimer, the term of this patent is extended or adjusted under 35 U.S.C. 154(b) by 1239 days.

(21) Appl. No.: 11/496,062

(22) Filed: Jul. 29, 2006

(65) Prior Publication Data

US 2007/0193580 A1    Aug. 23, 2007

(30) Foreign Application Priority Data

Aug. 1, 2005   (DE) .................. 10 2005 036 611
Mar. 28, 2006  (DE) .................. 10 2006 014 751

(51) Int. Cl.
*A61M 11/00* (2006.01)

(52) U.S. Cl. .......... 128/204.14; 128/203.16; 128/203.17

(58) Field of Classification Search ............. 128/204.14, 128/200.24, 203.16, 203.17, 204.17, 203.27, 128/203.12, 200.11
See application file for complete search history.

(56) References Cited

U.S. PATENT DOCUMENTS

| | | | | |
|---|---|---|---|---|
| 3,690,317 A | * | 9/1972 | Millman | 128/200.16 |
| 4,261,353 A | * | 4/1981 | Bartels | 128/200.11 |
| 5,673,687 A | * | 10/1997 | Dobson et al. | 128/204.14 |
| 6,115,539 A | * | 9/2000 | Cohn | 392/402 |
| 6,644,311 B1 | * | 11/2003 | Truitt et al. | 128/204.22 |
| 7,413,173 B2 | * | 8/2008 | DiMatteo et al. | 261/142 |
| 2005/0178383 A1 | * | 8/2005 | Mackie et al. | 128/203.16 |
| 2007/0169776 A1 | * | 7/2007 | Kepler et al. | 128/200.23 |

* cited by examiner

*Primary Examiner* — Steven O. Douglas
(74) *Attorney, Agent, or Firm* — Lucas & Mercanti, LLP; Klaus P. Stoffel

(57) ABSTRACT

A ventilator with integrated breathing air humidifier has at least two defined air pathways provided in the breathing air humidifier, wherein the breathing air humidifier is installed and fixed on a horizontal surface of the ventilator. The ventilator with integratable breathing air humidifier has a breathing air humidifier with at least a top part and a bottom part, wherein a water reservoir is provided in the bottom part, and wherein the top part cannot be removed from the bottom part when the unit is in at least one operating mode. The ventilator may have an air humidifier with at least one water reservoir, and at least one filing device for the water reservoir in the breathing air humidifier, wherein the filing device can be operated with one hand and/or opened with one hand.

32 Claims, 31 Drawing Sheets

VENTILATION DEVICE

BACKGROUND OF THE INVENTION

1. Field of the Invention

The present invention relates to a ventilation device which either provides a patient with partial breathing assistance or does all the breathing for the patient.

2. Description of the Related Art

These units for supplying breathing gas are usually based on a certain air flow concept, which influences the breathing gas and changes the influence of the breathing gas on the device in the desired manner.

In many cases, a blower motor serves as the gas source. This makes the device independent of other, stationary gas sources. The ambient air is drawn through a filter, arrives in the blower housing, and, for preparation with oxygen and/or moisture, is administered to the patient. In the devices according to the state of the art, furthermore, a clumsy and unattractive method is used to connect the humidifier to the basic unit. This also increases the size of the unit unnecessarily. The filling of the humidifiers also has a direct influence on the geometries and air supply properties of the device.

In many cases, the most effective way of influencing the amount of sound and noise produced is to isolate the blower from the rest of the device. In most devices, this idea is realized in a cumbersome, complicated, and inadequate manner.

The design embodiments and variants explained in detail below can be used alternatively or supplementally with respect to each other. In particular, each individual inventive idea can be realized independently of each of the other inventive ideas. A combined realization, however, leads to additional advantages, which have positive effects on the construction, size, ease of use, safety, and noise generation of the unit and thus positive effects on the entire system.

To supplement the following explanations, various additional explanations will be found directly in the drawings. The disclosure content of the present patent application comprises, in particular, both the written explanations of the drawings and also the design variants illustrated in the drawings but not explained in the following text.

SUMMARY OF THE INVENTION

The task of the invention is to provide a device which is suitable for CPAP, bi-level, APAP, titration, home, emergency, and hospital ventilation by either invasive or noninvasive means.

The air present in the atmosphere is drawn in by a blower integrated into the unit. The air thus passes through at least one filter, which separates the particles present in the air.

The air then arrives in a semi-enclosed sound-damping box, which is located inside a device for supplying breathing gas and which has a high-pressure area and low-pressure area.

Another embodiment provides a structure consisting of at least two modules. If central modules are present, the outer modules are fastened to them by screws and thus clamp them in position. This design can be realized by means of latching elements and/or screws, which pass through all of the modules.

Damping materials between the modules can be easily clamped and held in place by tongue-and-groove profiles.

Because at least one area and/or one side of the box is open, air could freely escape from the box through this opening. This is prevented by a simple seal of foam material. The foam fulfills the functions of sealing the sound-damping box, of damping the sound, and also of at least partially supporting the sound-damping box. The sealing action can be achieved simply by the application of pressure, by clamping, by adhesive bonding, and/or by screwing the box onto the foam. A seal is preferably provided both in the low-pressure area and in the high-pressure area of the sound-damping box.

The sound-damping box is thus characterized by simpler and lower-cost construction.

An opening is also provided in the box for the cable coming from a blower. The box is preferably formed by the cooperation between two modules.

The air flow can proceed between or in these modules and therefore proceeds in at least two planes, preferably three planes: the intake or low-pressure plane, the blower plane, and the discharge or high-pressure plane.

The functions are thus divided vertically into the individual planes. A "plane" is defined here as a long, flat, elongated space.

The air flow planes can be connected to each other by channels/structures. The channels/structures are preferably essentially perpendicular to the planes and can project far into the next plane or into at least one plane which bridges the next plane.

The air flow path is also intentionally laid out so that the direction of air flow is diverted at least twice by 80°±10°, once from vertical to horizontal and once from horizontal to vertical. This diversion of the air helps considerably to minimize the production of noise.

In an especially preferred embodiment, this effect is linked with another possibility of sound damping and/or is integrated into the sound-damping box. First, the previously mentioned diversions, preferably of 90° or 180°, of which there should be as many as possible, are used to deflect the air onto baffle plates, which thus at least partially absorb the sound; second, as many alternations as possible between cross-sectional constrictions and cross-sectional expansions in the form of channels, openings, and/or exit areas between openings and baffle plates are used.

In an especially preferred embodiment, this baffle plate can also be provided with a special sound-damping surface and/or lined with various materials.

Second, as many alternations as possible between cross-sectional constrictions and cross-sectional expansions in the form of channels, openings, and/or exit areas between openings and baffle plates are integrated into the sound box.

To achieve a further reduction in the amount of sound produced, an alternation between air-conducting and sound-damping areas is provided. The air-conducting and sound-damping areas are defined by openings, which result from the geometries of other components of the sound-damping box: screw channels, the blower, the external boundaries of the box, the blower mounting, the intake connectors, the intake filter, the discharge opening, etc.

Because the existing geometries of integral components of the sound-damping box are used to form the air flow guides and sound-damping areas, the volume can be kept relatively small.

For example, when screw channels are provided inside the planes, the air flow is adapted aerodynamically in such a way that the number of flow separations, which can lead to noise, is reduced to a minimum.

In a preferred embodiment, the blower is located as close to the center of the sound-damping box as possible. This offers optimum conditions over the widest possible area for influencing the sound produced by the blower and of damping it with respect to the outside.

In a preferred embodiment, the blower and the blower mounting are located within a central plane, the blower preferably being suspended from above. This plane is itself surrounded by sound-damping material. In addition to the preferred method of suspending the blower from above by means of elastomeric material, however, it is also possible to support it from underneath and/or from above with the help of springs, elastomeric material, and/or foam to ensure that the blower is effectively isolated from the box.

In addition to its suspension, the blower has another connection to the sound box in the form of at least one hose. This connection, however, is selected with respect to form and material so that the blower is isolated from the sound-damping box.

The preferred method of mounting the blower is to suspend it by means of elastomeric hangers in such a way that it has freedom of movement in three dimensions.

Thus, with the concept presented here, the blower is thus isolated from the equipment housing in at least one way and preferably in two: The sound-damping box is isolated by being mounted on foam and sealing material and also by the use of an elastomeric hose to conduct the air from the sound-damping box to a component permanently connected to the housing.

In addition to or in place of the measures described above, the blower can be isolated from the sound-damping box by means of the mounting methods cited above and by means of at least one elastomeric tube for conducting the air. Together with the elastomeric hangers, of which at least two are provided, this tube then serves not only to isolate the sound but also to support the blower.

The elastomeric tubes are connected to their mating parts by folding in the ends and pushing them over the mating profiles of the other parts to which they are to be joined.

The box can be fabricated of any desired material, preferably of plastic or metal.

The elastomers used to support/suspend the blower should have viscoelastic properties and thus have energy-absorbing properties in addition to their elastic properties. This makes a key contribution to the reduction of the transmission of sounds and vibrations. As previously explained, the blower can be supported from underneath or preferably from above.

Through proper selection of the material and design of the suspension and support elements, the blower can be installed quickly and easily in the sound-damping box.

Installation is made possible by the integration of a guide element and a shoulder/undercut on each of the hangers. During the installation process, the tip of the hanger makes it easy to guide it through a suitable bore; the blower then engages with the undercut and can be detached only by partially destroying the mounting.

At the same time, the hangers seal the bores and thus also seal off the two adjacent planes from each other. A suspended mounting also offers the advantage that considerable relative movement is possible.

These movements are limited to the desired extent by additional elements, at least some of which are attached to the base of the hangers and around them. These deflection limiters prevent, for example, the blower from contacting the walls of individual modules of the sound-damping box.

As previously explained, a preferred support can consist of at least one elastomeric mounting element and at least one tubular air channel or tubular isolating hose, which can also consist of elastomeric material or of rubber-like material.

The selection of the design and material of the mounting elements largely determines the quality of the sound isolation.

After the air has entered the unit through the intake and after the sound has been reduced by the sound-damping box, the air arrives in the stationary housing shell part of the unit.

To guarantee that the patient is provided with gas under the best possible conditions in terms of respiratory physiology during the treatment, it can be helpful to use a humidifier. When desired, this unit can be connected to the previously described components, preferably downstream from them.

To ensure that the humidifier is positioned precisely and that it is integrated optimally into the base unit, the three possible directions in which the humidifier can move are limited by various elements of the base unit.

The first dimension is limited by the facing contact planes, namely, the bottom plane of the humidifier and an upward-facing, also horizontal plane of the base unit.

The second dimension is limited by the presence of at least one round element, preferably two round elements, both of which can be components of the humidifier or of the base unit. To prevent the humidifier from tipping as it is being inserted into the base unit, the humidifier is provided with guide rails.

In a preferred embodiment, the round elements consist of a tubular connecting piece of the air flow guide system, an air inlet, and a self-limiting heating rod, designed to produce an electrical connection, which projects into the bottom part of the humidifier, is immersed in water, and is responsible for heating the water in the filled humidifier.

The isolating element between the sound-damping box and the base unit serves simultaneously as sealing material for the connection between the air intake and the humidifier. The humidifier has at least one centering element, preferably designed as a rail, to prevent it from tipping as the cover cap is being introduced into the base unit. The base unit has guide slots.

The third dimension is limited by the insertion of a connecting element through the base unit and through the humidifier. The connecting element connects the air flow to the humidifier at one end and to the patient hose at the other end. The air pathways thus created are not parallel. In particular, the inlet to the humidifier and the outlet from it are arranged at an angle of preferably $80°\pm10°$ to each other.

To maintain a high level of moisture in the air, various air flow pathways are conceivable. The air is conducted through the unit to the bottom part of the humidifier, from which it rises vertically upward through an air-carrying profile. It then mixes as desired with the highly humidified air of the humidifier and carries a portion of the humidity back into an additional profile, which guides the air vertically downward. The humid air then passes through the connecting element and thus finally reaches the breathing hose and the patient.

The air flow guide profiles can consist of two separate, adjacent pipes (FIG. 10) or of two concentric pipes (FIG. 11) with a central air inlet tube. A nozzle insert is installed on this air inlet tube to guarantee optimal, uniform distribution and uptake of the humidity by the flow of air.

In an especially preferred embodiment, the air enters and leaves through a centrally installed pipe with an implemented wall to separate the inlet from the outlet.

The air introduced into the humidifier first strikes a baffle plate. In conjunction with a separating plane and a mushroom-shaped hood, the air is thus diverted directly onto the surface of the water to ensure that the air absorbs a large amount of moisture.

These elements are seated in the upper part of the humidifier. The separating plane prevents a short-circuit from forming between the incoming and outgoing air, which would prevent the air from becoming humidified.

The incoming and outgoing air profiles should be as close to the center as possible to prevent any possible intrusion of water into the openings, especially into the opening of the incoming air channel. In addition, the tilt and height of the opening has an effect on the likelihood that water will be able to enter the openings, especially when the unit is resting at an angle, which would thus affect the rebound behavior of the air flow.

In conjunction with the separating plane of the upper part and the air flow guide profiles of the humidifier, it is also advisable to provide measures to prevent the top part from being twisted on the bottom part.

In addition to the previously described elements, the top part of the humidifier has additional inventive elements, which improve the air flow guidance, safety, and ease of use of the unit for supplying breathing gas.

It is advantageous that the mushroom-shaped hood over the air flow guide openings prevents the intrusion of water into the unit when the humidifier is being filled.

The mushroom-shaped hood or collar is arranged so that it is concentric with respect to the inlet/outlet tube in the top part to prevent spray water from entering the tubes, especially from entering the inlet. The collar of the outlet is not as tall, so that, when the unit is resting at an angle and the humidifier tank is full, the positive pressure built up in the unit cannot cause water to enter the air outlet and pass via the air discharge line into the hose. In addition, the collar guides the air directly onto the surface of the water.

On the side which guides the air inward, the mushroom-shaped hood is provided with a larger collar than it is on the side which guides the air outward, both to prevent water from entering the unit and to prevent water from escaping when the unit is resting at an angle.

The humidifying space is sealed off by the top part and a seal. In a preferred embodiment, the seal is designed as an O-ring. In this case, the standard radial sealing method is not used; instead, an axial seal is used with the help of a circumferential shoulder on the top part (shoulder on the inside) and another shoulder on the bottom part (shoulder on the outside). The top part is dimensioned so that it is easy for the user to upend it over the bottom part. The sealing element is therefore not squeezed in the radial direction but rather remains on the actual axial sealing surface. The ring-shaped sealing element acts as an assembly aid for the user and prevents the sealing element from being pushed out of its radial position.

When the humidifier is detached from the unit, it is kept closed by a bayonet joint. When the humidifier is mounted on the unit, the top part of the humidifier cannot be untwisted from the humidifier nor twisted onto the humidifier. This is provided according to the invention to minimize the likelihood that water could enter the unit during the process of filling the humidifier. Such entry could occur by mistakenly pouring water into the profiles while the bottom part of the humidifier is open. This safety measure to prevent the top part of the housing from being taken off is realized by a positive connection with the ventilator.

So that the humidifier can be filled while it is installed on the unit, a stopper is provided on the top part. According to the invention, this can be operated with only one hand, which significantly improves the ease of use in comparison with previous types of closure. This is achieved through the use of a pretensioned element, which, when operated (opened), automatically allows the stopper to flip into the fully open position.

The opened state of the stopper is free of tension; in the closed state, the stopper is under tension. For this purpose, slight pressure is exerted on the lever-like stopper to overcome both the pretensioning force and the sealing force.

In some groups of patients, namely, those who do not complain of dryness of the mouth or of the airways, the use of a humidifier can be omitted. So that the unit can be opened and used even without the humidifier, a dummy humidifier is used, which is inserted into the base unit in the same way as described above.

If a dummy humidifier is used, the heating rod is not necessary and is replaced by a blind connection, which closes off the opening in the unit and protects the electrical contacts for the heating rod from environmental influences.

The connectors for connecting to the air outlet and the heating rod of the base unit are also designed as parallel connections. The first dimension is again limited by the facing horizontal planes, i.e., the bottom of the dummy humidifier and the upward-facing, horizontal surface of the base unit.

The second dimension is inhibited by the connection of least one, preferably two round elements to the base unit. The third dimension is inhibited by the introduction of a connecting element through the basic unit into the dummy humidifier.

The stopper also serves to reduce the mask sound, because the stopper has a relatively large space for expansion, in which, in a preferred embodiment, additional cross-sectional constrictions and expansions and sound-damping materials can be installed.

To reduce the mask sound even more, the size of the stopper can be increased and provided with several such elements. The stopper has at least one centering element, preferably designed as a rail, to prevent the cap from tipping as it is being introduced into the base unit. The base unit has guide slots.

The isolating element has an additional function, namely, that of a seal with a sealing bead for the air intake of the humidifier or dummy humidifier.

Until now it has not been possible to detach the hose quickly from the unit with only one hand. By means of the connecting element mentioned above, however, a standard ventilator hose can be attached to the unit easily, quickly, and with only one hand.

This element has a Bernoulli compensator. With the help of a constriction, this element simulates the behavior of the breathing hose, especially the resistance of the breathing hose, so that, after the pressure has become reduced in the constriction, it is equivalent to the pressure at the mask of the patient. This eliminates the need for a pressure-measuring hose leading to the patient.

The pressure present in the constriction of the connecting element is conducted through an opening in the connecting element, preferably a slot, and via a pressure-measuring connecting piece leading to a pressure sensor positioned in the unit.

The pressure-measuring channel is located in the same place regardless of which of the two different elements (humidifier or dummy humidifier) is present. The two elements do not have any relevant effect on the measurement, because the measuring site is located as far away as possible from them, at the outlet of the unit. The geometries present in the area of the connecting element are identical.

The connecting element has at least one seal, preferably two O-rings, which, with respect to the flow of gas, are upstream and downstream of the pressure opening. One seals off the unit from the outside and the other seals off the pressure measurement connecting piece from the interior of the unit, because pressure gradients near the Bernoulli element can short-circuit the air flows and thus interfere with the possibility of a correct measurement.

The opening which produces the connection between the pressure space in the area of the constriction and the pressure sensor in the unit is preferably at the top, because otherwise condensate would probably accumulate in the circumferential groove and could affect the pressure measurement.

In another preferred embodiment of the connecting element, an anti-twist device which cooperates with the base unit is attached to the element. The anti-twist device makes it easy to join the element to the mating component and is preferably designed as a triangle. The tip pointing in the joining direction serves simultaneously as a centering/positioning element for the connecting element.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE INVENTION

Figure 1:
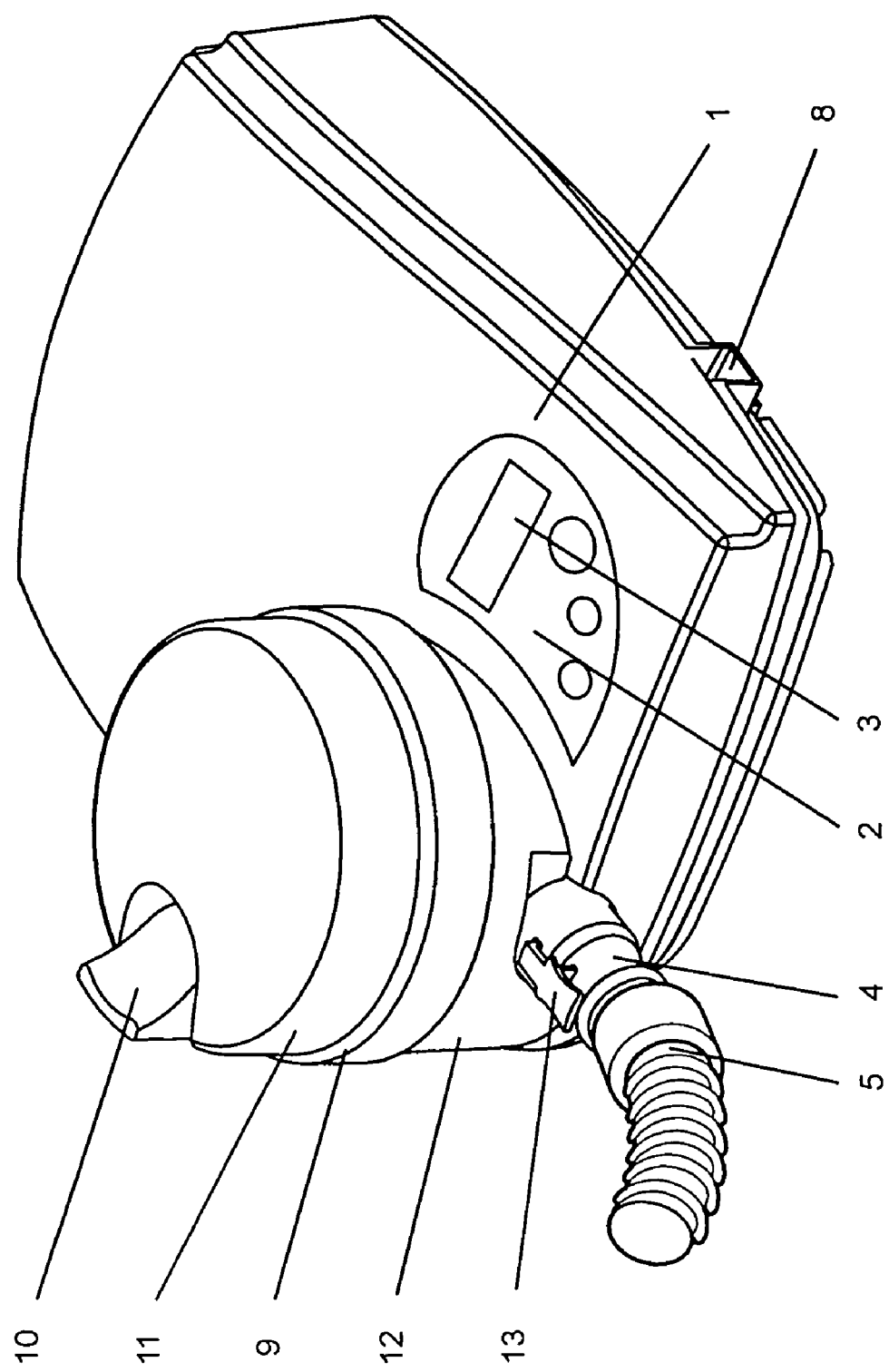
FIG. 1 is a perspective view of a ventilation device.

FIG. 1 shows the basic design of a ventilation device. In the equipment housing (1) with the control panel (2) and display (3), a breathing gas pump is installed in the interior of the unit. A connecting hose (5) is connected to the ventilator by means of a connecting element (4). The connecting element (40) can be connected to the ventilator device quickly and easily. An additional pressure-measuring hose (not shown), which can be connected to the equipment housing (1) by means of a pressure inlet connector (not shown), can extend along the connecting hose (5). The equipment housing (1) has an interface (8) to allow the transmission of data. At the end the connecting hose (5) facing away from the equipment housing (1), an exhalation element (not shown) is provided.

To prevent the patient's airways from drying out, it is has been found advisable to humidify the breathing air, especially during long phases of ventilation. These humidifications of the breathing air can also be realized in other applications. To humidify the air, adaptable breathing air humidifiers (9) are usually used, which are installed in the air pathway between the ventilator and the patient. The breathing air humidifier consists of a top part (11) and a bottom part (12). The breathing air humidifier has at least one water filling port, which is in the area of the top part (11).

In addition, an oxygen feed valve can be adapted to supply the user with an increased amount of oxygen along with the breathing gas.

At the end facing away from the ventilator, the connecting hose can be connected to a patient interface, which can be designed as a nasal mask. A hood can be used to hold the mask in position on the patient's head. On the side facing the connecting hose, the breathing mask has a connector piece.

Figure 5:
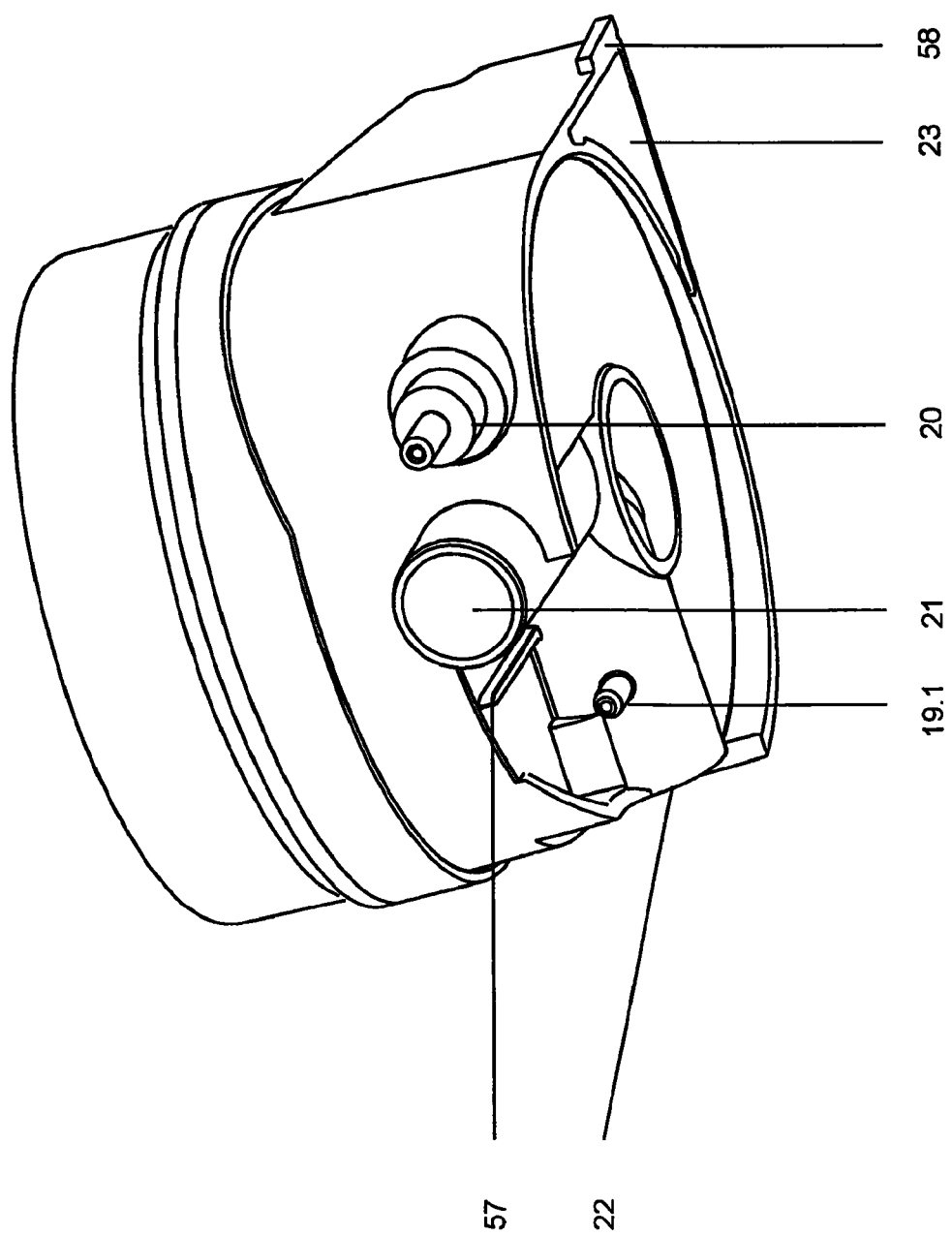
FIG. 5 is a perspective bottom view of the breathing air humidifier.

The top part (11) has a curved edge, which can be seen especially clearly in FIG. 5, the curvature of which conforms to the curved contour of the top surface of the equipment housing (1). After the breathing air humidifier has been mounted on the equipment housing (1), the top part (11) can therefore not be twisted off the bottom part (12). This prevents the breathing air humidifier from being filled improperly.

Figure 2:
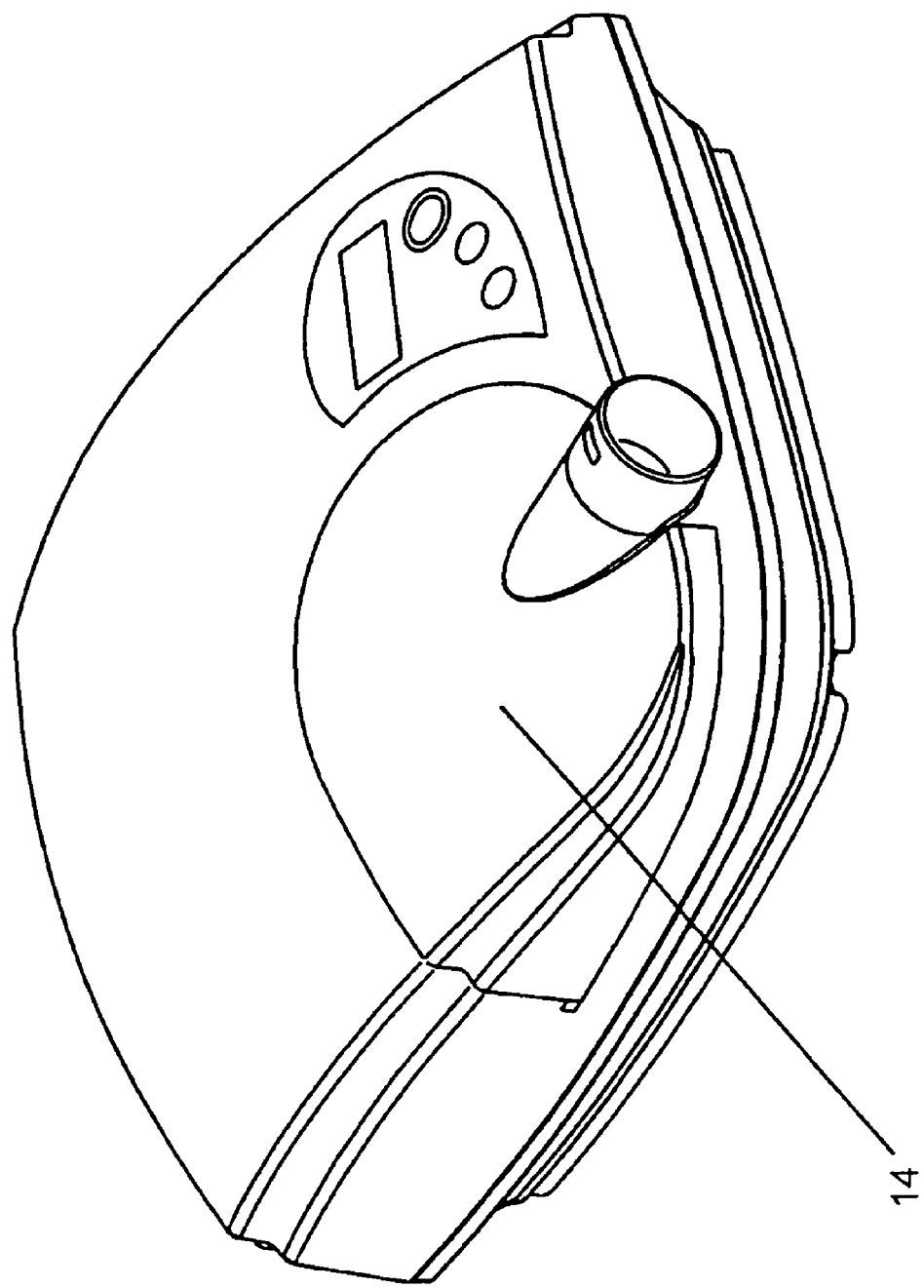
FIG. 2 is a perspective view of the ventilation device of FIG. 1 shown with a cover in place of a breathing air humidifier.

In the area of the receptacle for the breathing air humidifier (9), it is possible as an alternative, as shown in FIG. 2, to install a cover (14) in place of the breathing air humidifier (9). This cover engages positively with the top and side areas of the base unit, merging with the external contours of the unit and thus forming a closed surface.

The cover (14) serves not only an air guidance function but also a pneumatic function. Because air is conducted through the interior of the cover (14), a sound-damping function is achieved. When installed, the breathing air humidifier also helps to reduce the noise level.

Figure 3:
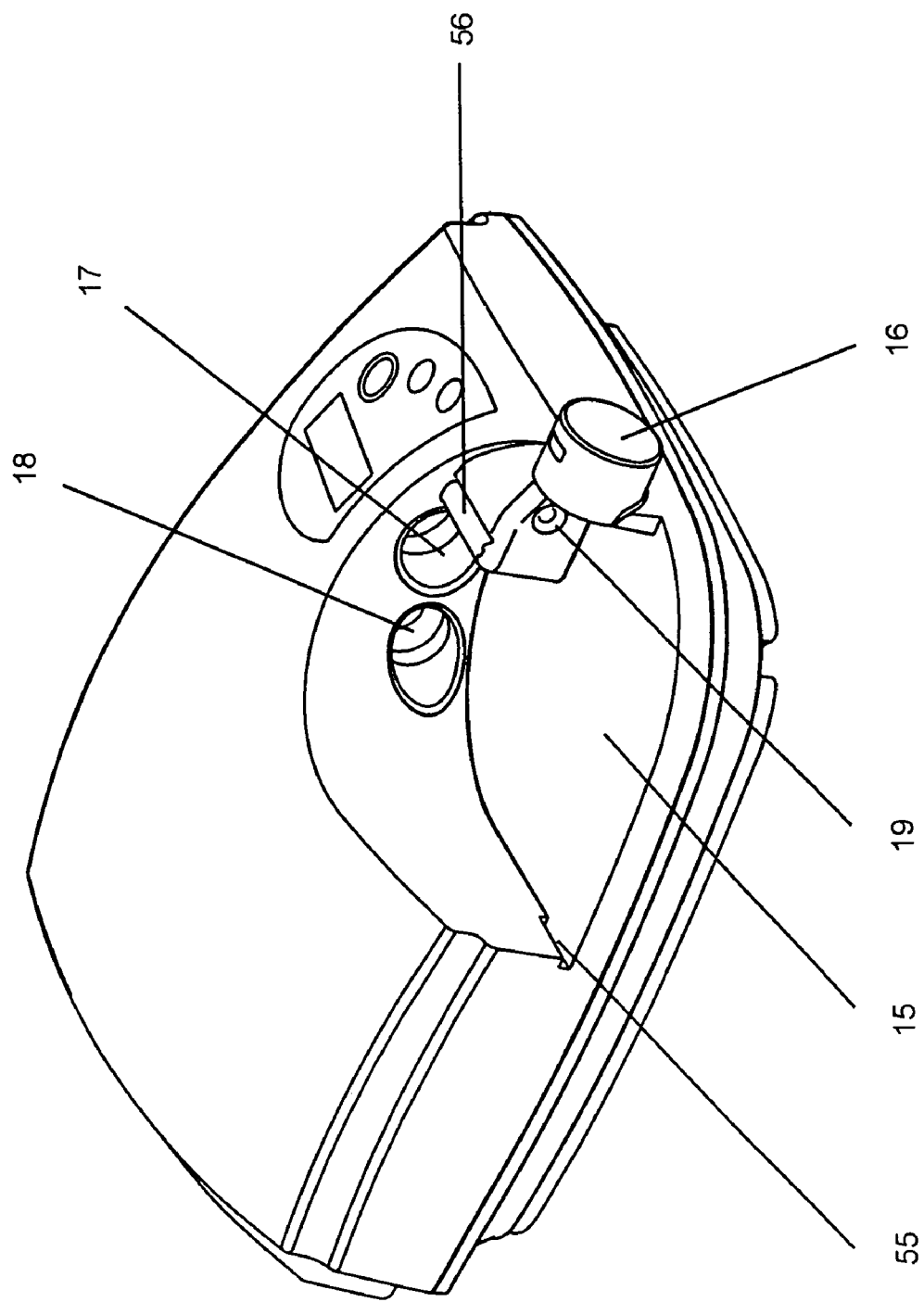
FIG. 3 is a perspective view of the ventilation device showing the receptical for the breathing air humidifier.

The receptacle (15) for the breathing air humidifier, as shown in FIG. 3, is essentially parallel to a support surface of the unit. The breathing air humidifier (15) is inserted essentially sideways onto and/or into the unit. Installation is facilitated by the two guide aids (55, 56); these center the breathing air humidifier during the insertion process, so that the air outlets of the unit (17) and the power supply (18) match up with the humidifier.

By giving the receptacle for the breathing air humidifier a rounded form, which is not, however, symmetrical, and by providing the breathing air humidifier with a complementary shape, the direction and/or arrangement of the breathing air humidifier in the unit is defined. The breathing air humidifier is inserted with an exact fit into the receptacle provided specifically for the breathing air humidifier. As a result, a high degree of functional integration is achieved. Faulty installation is thus prevented. The breathing air humidifier cannot be twisted out of place in the unit.

The air outlet (17) from the unit and the power supply (18) for the breathing air humidifier are located in the receptacle (15) for the breathing air humidifier. A pressure-measuring connector (19) can also be seen. In the forward area of the unit, there is an opening (16), which serves to accept the connecting element (4).

Because of the way in which the pressure-measuring connector (19) is arranged, the pressure is therefore measured in the unit, but downstream (in the direction of air flow) of the humidifier. Any pressure losses in the area of the humidifier will therefore not affect the pressure measurement.

Figure 4:
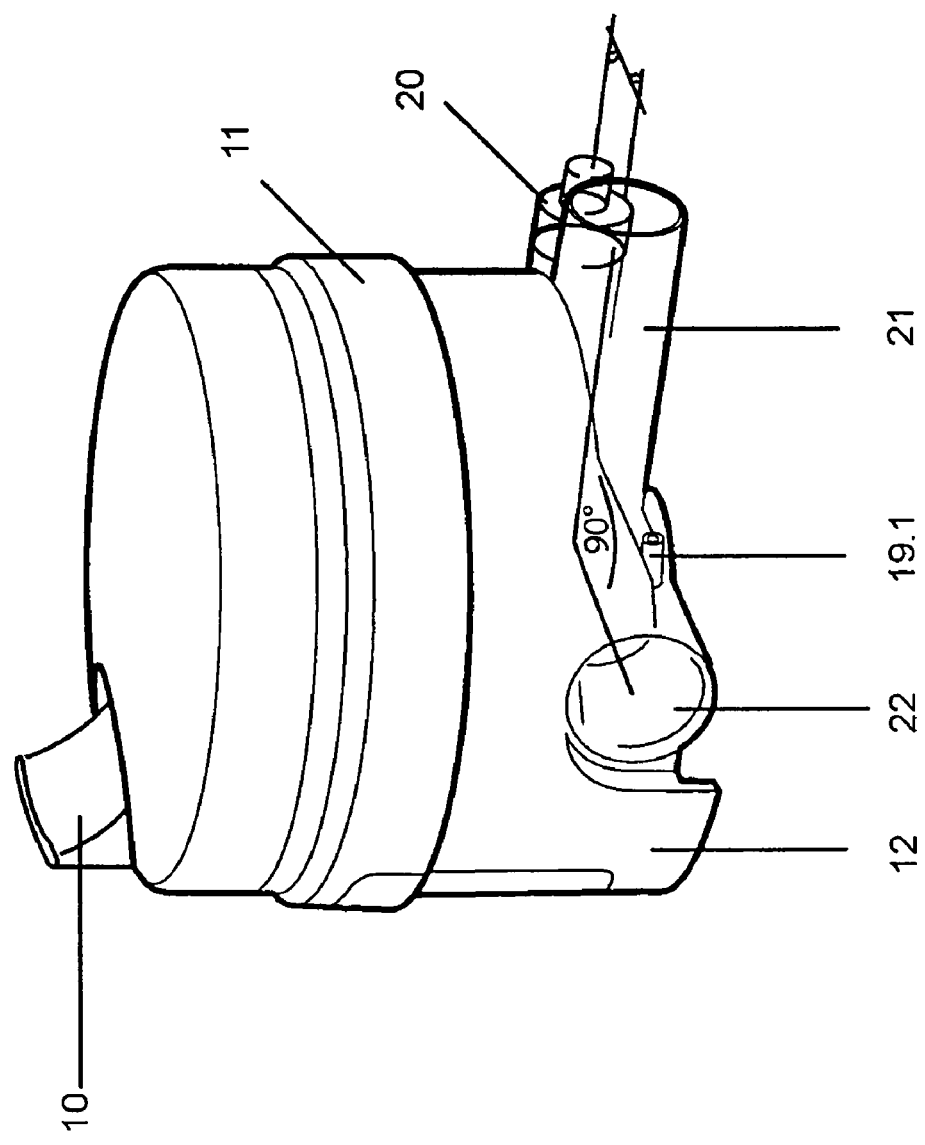
FIG. 4 is a perspective view showing the breathing air humidifier.

In the bottom part (12) of the breathing air humidifier, as shown in FIG. 4, the air inlet (21) and a plug contact (20) for the power supply of the breathing air humidifier are arranged essentially parallel to each other. The air outlet (22) of the breathing air humidifier is located not opposite the air inlet (21) in a straight line but rather at an angle of essentially 90° to the air inlet. In at least one operational state, the air inlet (21), the plug contact (20) for the power supply of the breathing air humidifier, and the air outlet (22) of the breathing air humidifier are located essentially underneath the water reservoir. A connector piece (19.1), which connects to the pressure-measuring connector (19), is located on one side of the air outlet (22).

FIG. 5 shows a view of the breathing air humidifier from below; the humidifier has been tilted slightly backward. The base of the humidifier is essentially rounded and provided with at least one corner (23). The corner prevents the humidifier from being twisted out of place on the unit, in that the base of the humidifier mates with the receptacle for the humidifier on the unit. A connector piece (19.1), which connects to the pressure-measuring connector (19), is located on one side of the air outlet (22).

The humidifier is held in place on the unit by means of plug-and-socket connections. That is, the air inlet (21) of the breathing air humidifier plugs into the air outlet (18) of the unit, and the power supply (20) of the breathing air humidifier plugs into the power supply (17) in the unit.

The humidifier can be adapted to the unit and made ready to operate in two steps. The humidifier is first guided horizontally onto the support surface of the unit, where the mating areas of the humidifier and of the unit define the proper joining direction. At least partial engagement between the mating areas, i.e., between the air inlet (21) and the power supply (20) of the breathing air humidifier with the air outlet (17) and the power supply (18) of the unit, holds the humidifier in position. Second, the humidifier is held and locked in its final position by the insertion and/or placement of the connecting element (4) into the opening (16) in the unit.

Two guide aids (57, 58) are also provided on the humidifier to ensure easy and secure installation. These guides engage with the two guide aides on the unit (55, 56).

Figure 6:
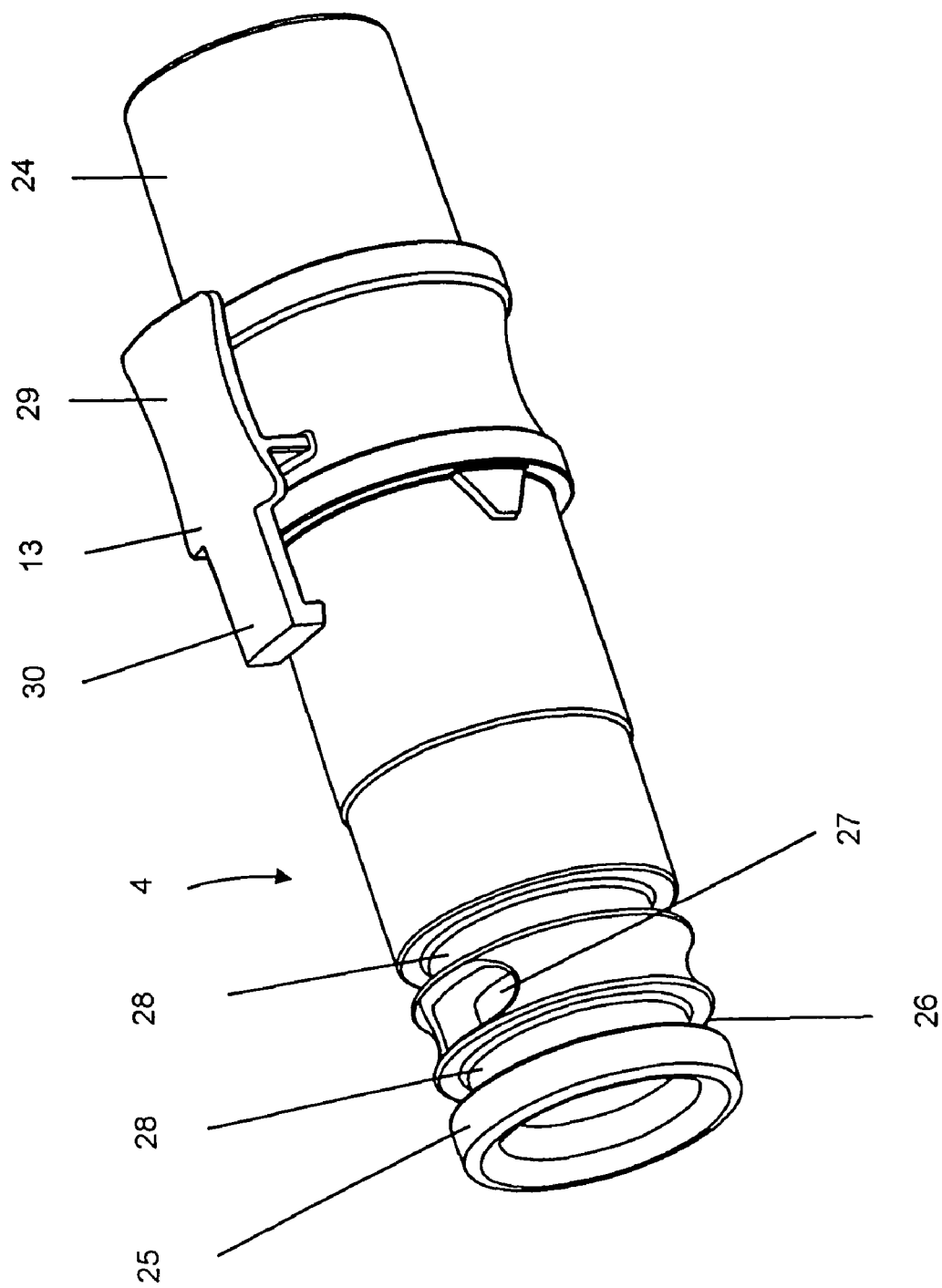
FIG. 6 is a perspective view of a connecting element for connection to an opening of the humidifier.
Figure 7:
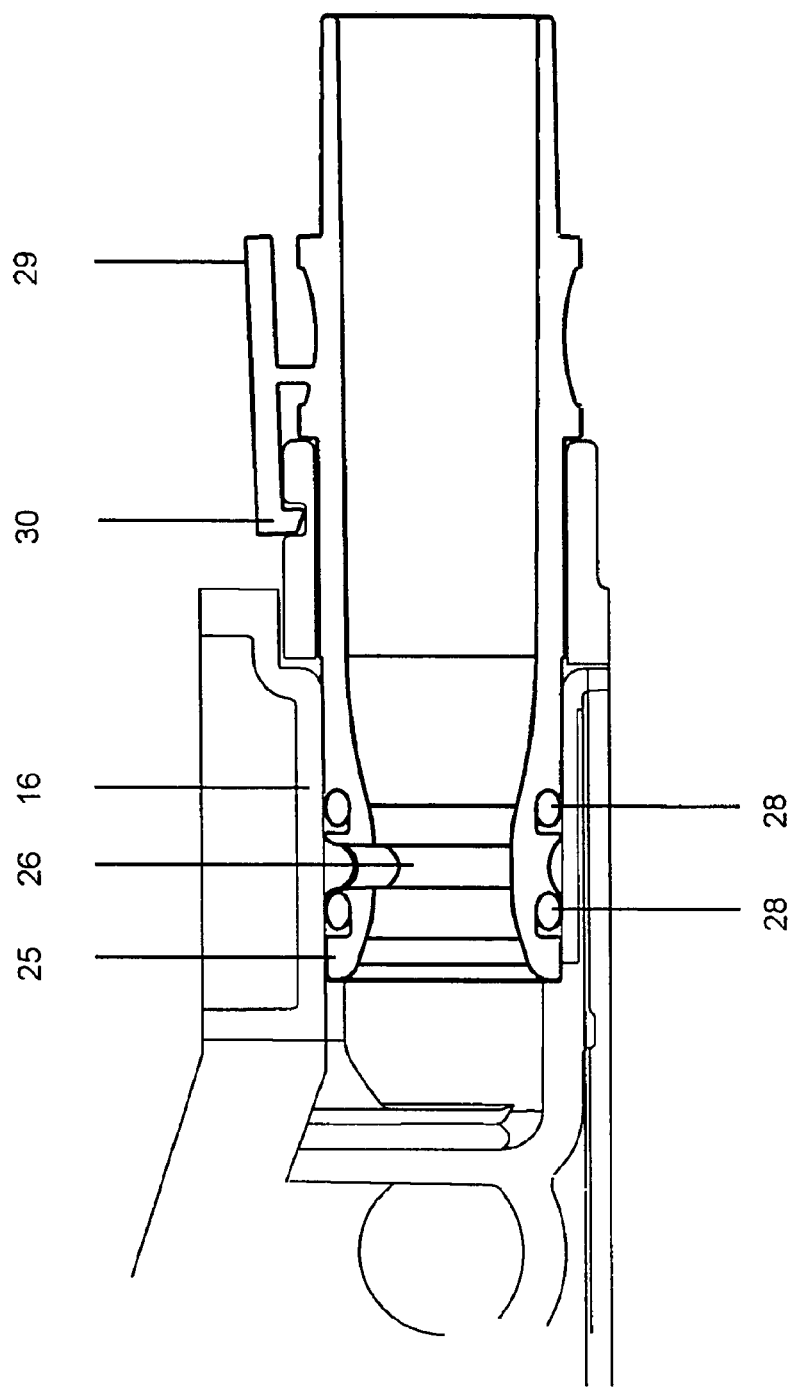
FIG. 7 is sectional view of the connecting element of FIG. 6.

FIGS. 6 and 7 show the connecting element (4). The connecting element (4) has an area near the unit (25) by which it is connected to the unit by way of the opening (16). At the opposite end, the element has a hose area (24), by which it is connected to the hose (5). By the application of pressure to the operating part (29) of the operating element (13), the functional part (30) of the operating element is moved. As a result, the connecting element (4) can be easily, quickly, and securely connected to the ventilator. In the area between the unit area (25) and the hose area (24), there is at least one seal (28), which can be designed as an O-ring or as a lip seal. In the connecting element, there is a taper (26), which has a smaller diameter than the connecting element. In the area of the taper there is a measuring opening (27).

The connecting element fulfills at least two of the following functions:
  1. it holds the humidifier on the unit;
  2. it forms an airtight passage between the humidifier and the hose;
  3. it fastens the hose to the unit and/or humidifier;
  4. it serves as a measuring site;
  5. it puts the device into operation;
  6. its air-conducting parts also partially hold the humidifier in place.

Figure 8:
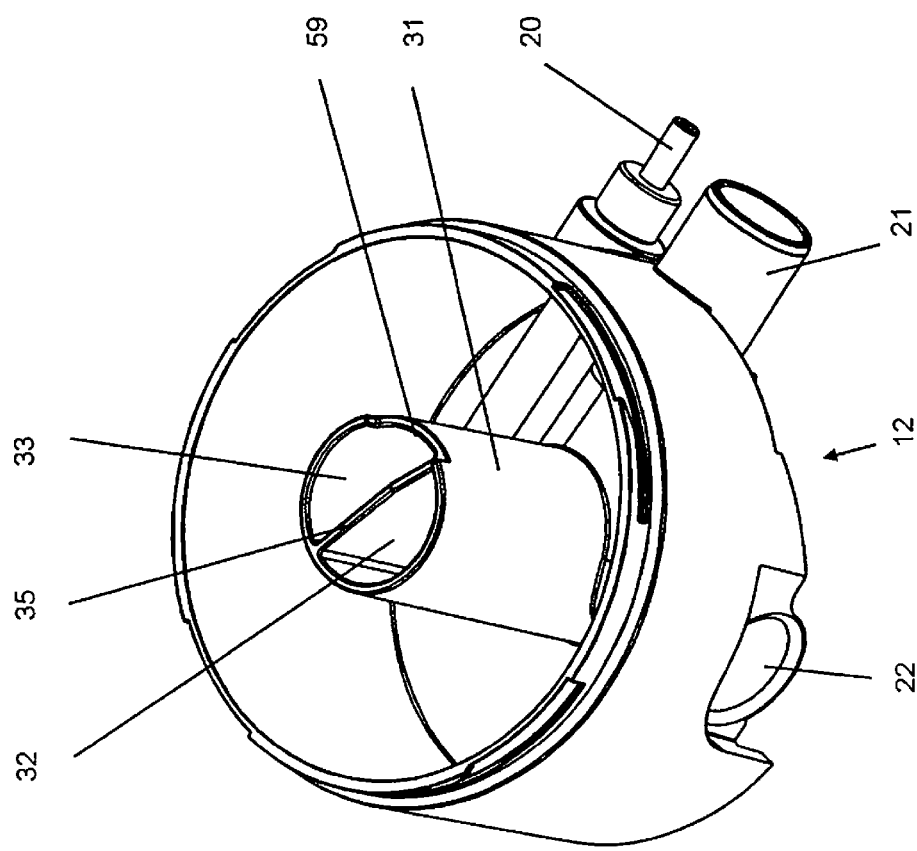
FIG. 8 is a perspective bottom view of the bottom part of the humidifier.
Figure 9:
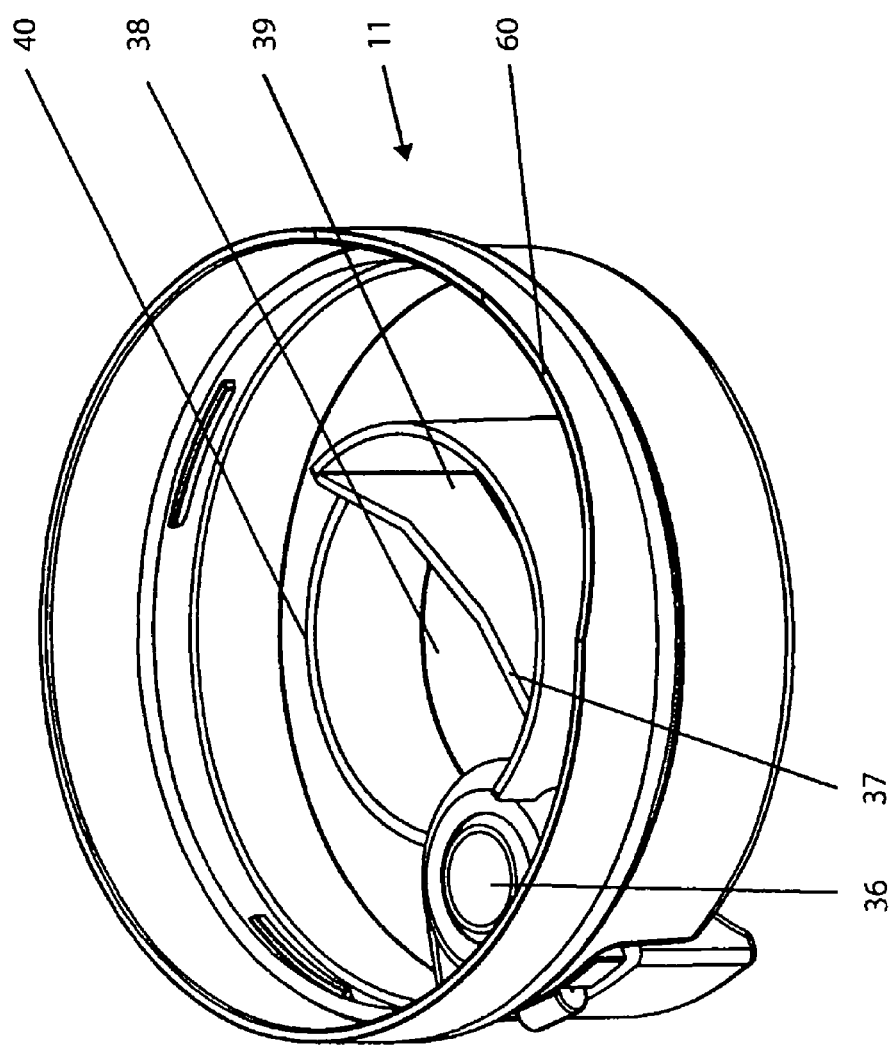
FIG. 9 is a perspective top view of the humidifier.

FIG. 8 shows the bottom part (12) of the humidifier, and FIG. 9 shows the top part (11). The bottom part serves essentially as a water supply chamber. The top part serves essentially to guide the flow of air and, in conjunction with the bottom part, creates the humidification space (41). The air coming from the unit to the bottom part is conducted through the air inlet (21), which is essentially at the bottom (34), to the center of the bottom part. There, the air conduit (31) bends upward around an angle of more than 60°, preferably around an angle of approximately 90°.

The air conduit (31) is divided in two by a continuous partition wall (35) and is open at the top. One part, serving as an air intake line (33), conducts the air coming from the unit into the top part (11) of the humidifier. After arriving in the entrance area, the air strikes the baffle plate (39), which is subject essentially to unhumidified air, and is conducted by at least one air guide structure (37) into the humidification space (41). The air guide structure (37) prevents essentially unhumidified air from being conducted directly to the air outlet (22). The structure fits into a recess (59) in the humidifier outlet and simultaneously serves as an anti-twist device for the top part of the humidifier.

The air which has become humidified during operation is now conducted by at least one air guide structure (37) to an area of the baffle plate (38), which is subjected essentially to humidified air. When the humidifier is assembled, a circumferential collar (40) is located above the upper end of the air conduit (31), serving a cap-like function. In cooperation with the air guide structure (37), which rests on the partition wall (35) with a sealing effect, the collar defines the path of the air through the humidifier. The collar (40) overlaps the upper edge of the air conduit (31). This overlap prevents water from surging into the air inlet and into the unit or into the air outlet and to the patient.

The air is guided through the humidifier essentially by vertical pipes, which are located essentially in the center of the humidifier. The opening is always located above the surface of the water.

Figure 10:
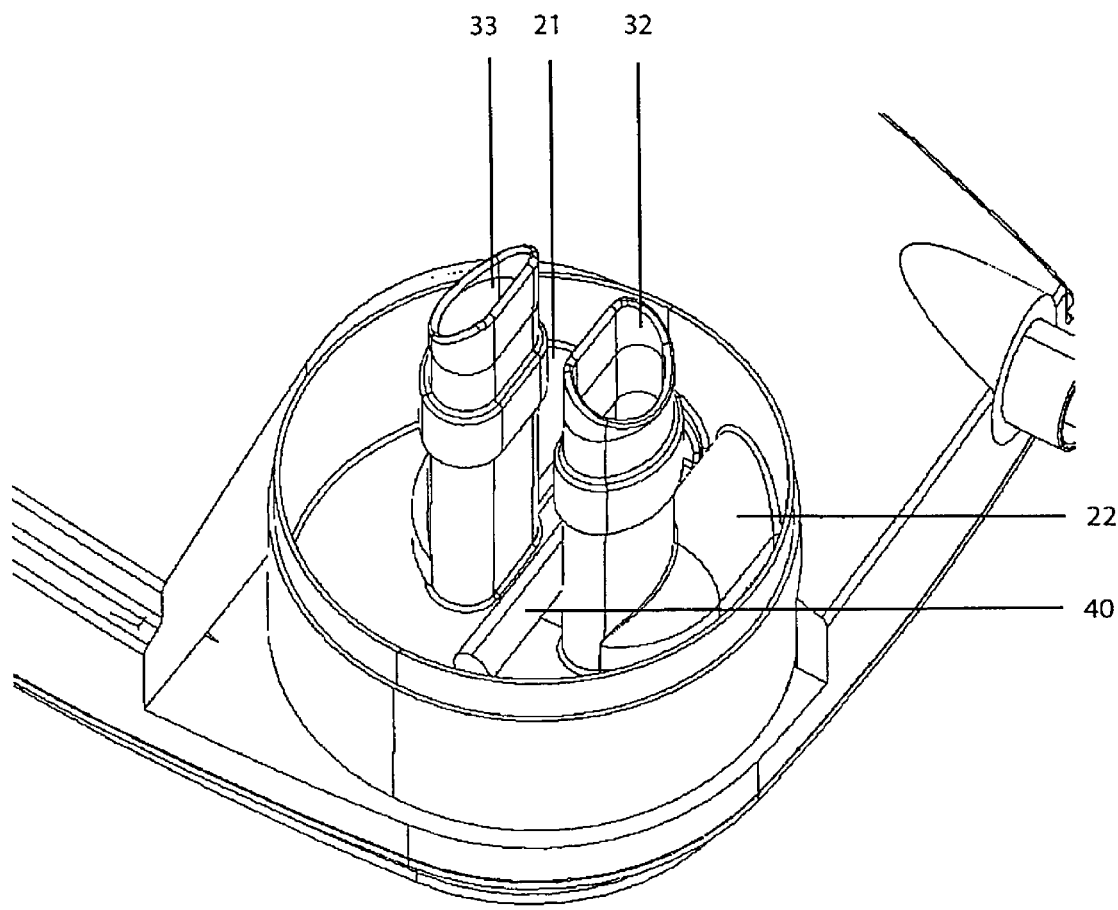
FIG. 10 is a perspective view of another embodiment of the humidifier.
Figure 11:
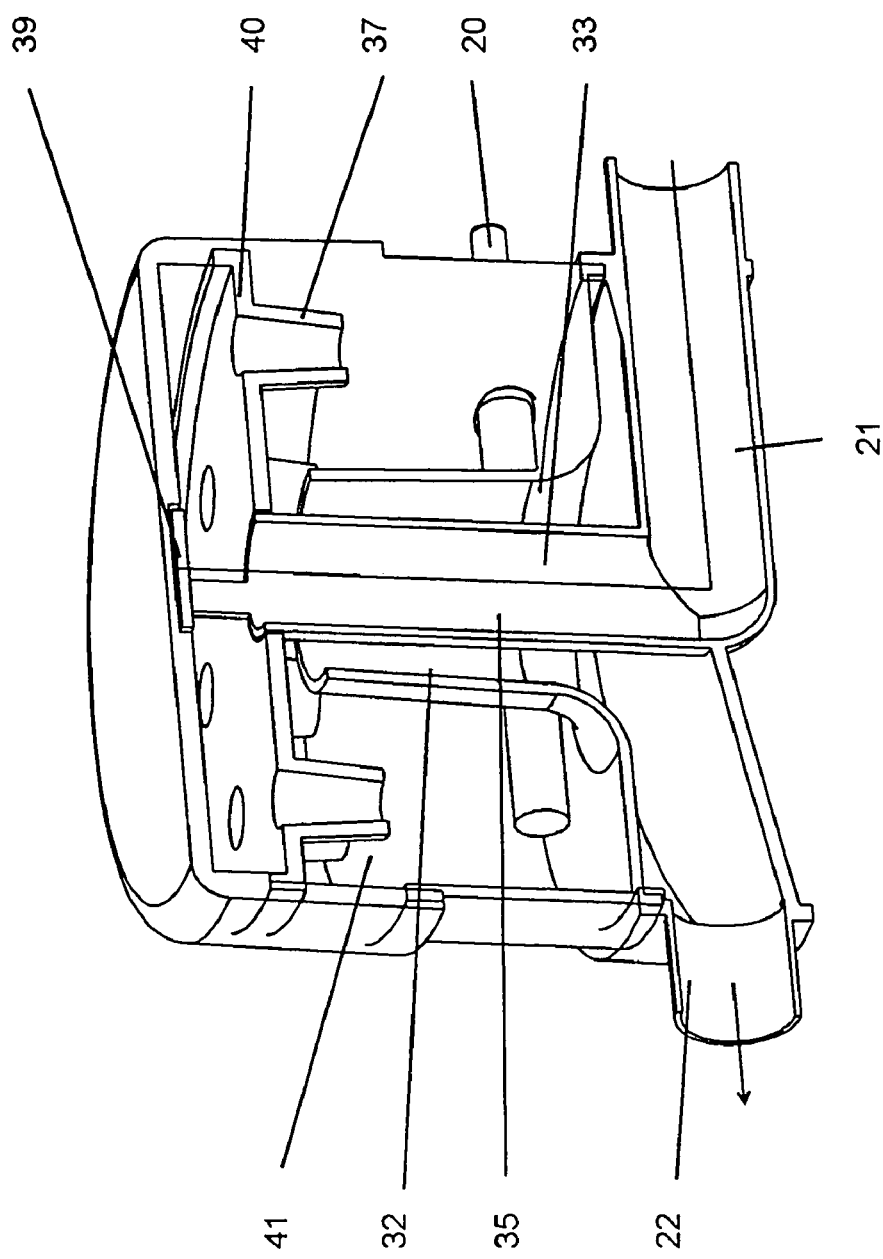
FIG. 11 is a partially broken view of the humidifier of FIG. 10.

According to the embodiment shown in FIG. 10, the air intake line (33) and an air discharge line (32) extend through two separate, chimney-like channels, which are essentially parallel to each other and are separated by a comparatively small gap.

In general, an essential design feature of the breathing air humidifier is to be seen in that, in the interior of the humidifier, chimney-like structures are provided to supply the air to be humidified and to carry away the humidified breathing air. The connections leading to the outside are all located in a lower area of the unit. This structure makes it possible to integrate the breathing air humidifier into the ventilator and avoids the need to fasten the breathing air humidifier onto the outside surface of the ventilator by means of a flange.

To prevent the top part (11) from being opened while the air-humidifier is attached, the opening (60) at the edge of the top part matches the shape of the housing, so that it is impossible to turn the top part (11), because at least a certain part of the opening (60) is designed to engage positively with the equipment housing.

In the top part (11), it is possible to see the water filling port (36), which can be accessed by way of the stopper (10).

Figure 12:
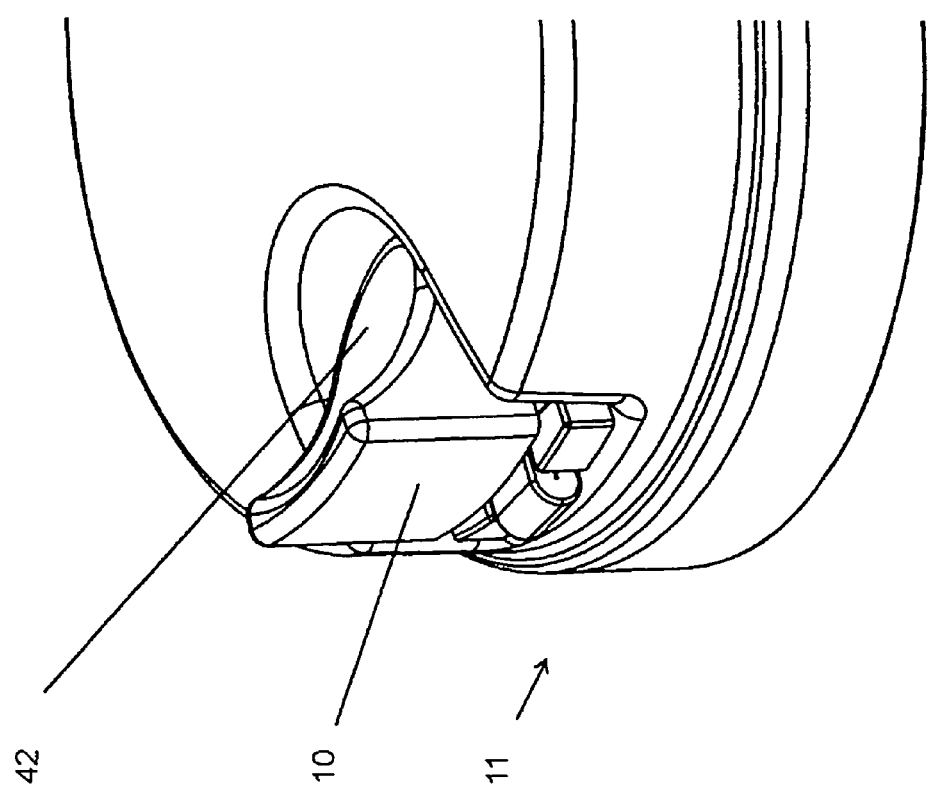
FIG. 12 is a partial perspective view of a stopper of the ventilation device.

As shown in FIG. 12, the stopper (10) for the filling port (36) is located in the top part (11), near the edge, for example. The stopper has in its upper area an operating surface (42). The operating surface is preferably slanted and, to improve its haptic properties, it has an irregular surface structure.

Figure 13:
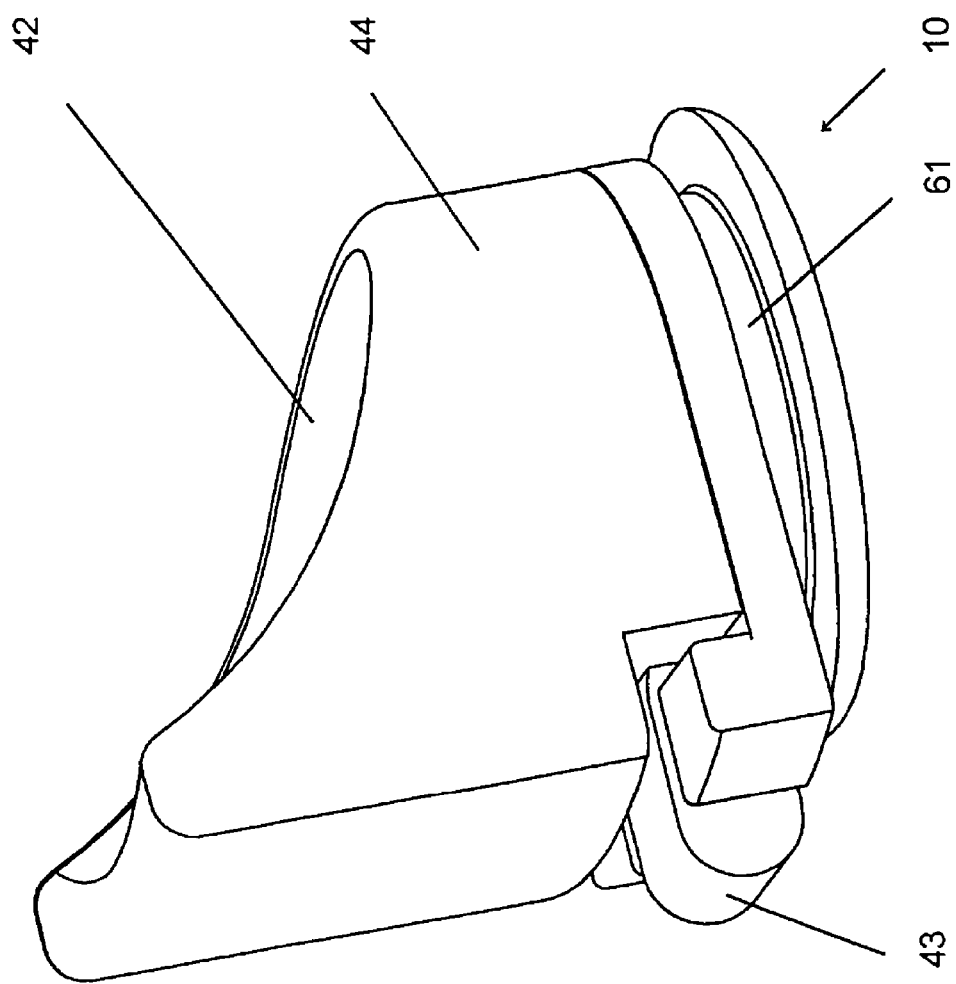
FIG. 13 is a perspective view of the stopper with a hinch.

As shown in FIG. 13, a spring-loaded hinge (43) is provided on the stopper. The hinge is preferably relaxed after the stopper has been lifted to open the filling port. The hinge is preferably under tension, however, as the stopper is lowered to close the filling port. The tension is calculated so that a light pressure exerted accurately on the operating surface is sufficient to open the filling port (see below).

The angle of the operating surface defines and directs the force applied by the user preferably in such a way that even a weak but accurately applied force is sufficient to cause the stopper to open the filling port.

The stopper is preferably made of a slightly elastic material; even more preferably, it is made of a rubber-like material. The circumferential groove (61) makes it possible to install the stopper easily on the top part (11).

In the ready-to-operate state, the top part of the humidifier cannot be removed. As a result, the goal is achieved that the humidifier cannot be filled in the wrong way, i.e., by improperly removing the top part.

The seal between the top part of the humidifier and the bottom part is provided by, for example, an O-ring. The seal is preferably axial, with radial guidance. It is also preferable to insert O-ring seals, which are guided radially but seal in the axial direction, in the area of the base unit.

It is especially preferable to use lip seals wherever pressures of more than 4 mbars can occur in the area of the humidifier and/or of the base unit. The applied gas pressure pushes the lip seal with a sealing action against sealing surfaces, which are located, for example, in the area between the top part and the bottom part of the humidifier.

Figure 14:
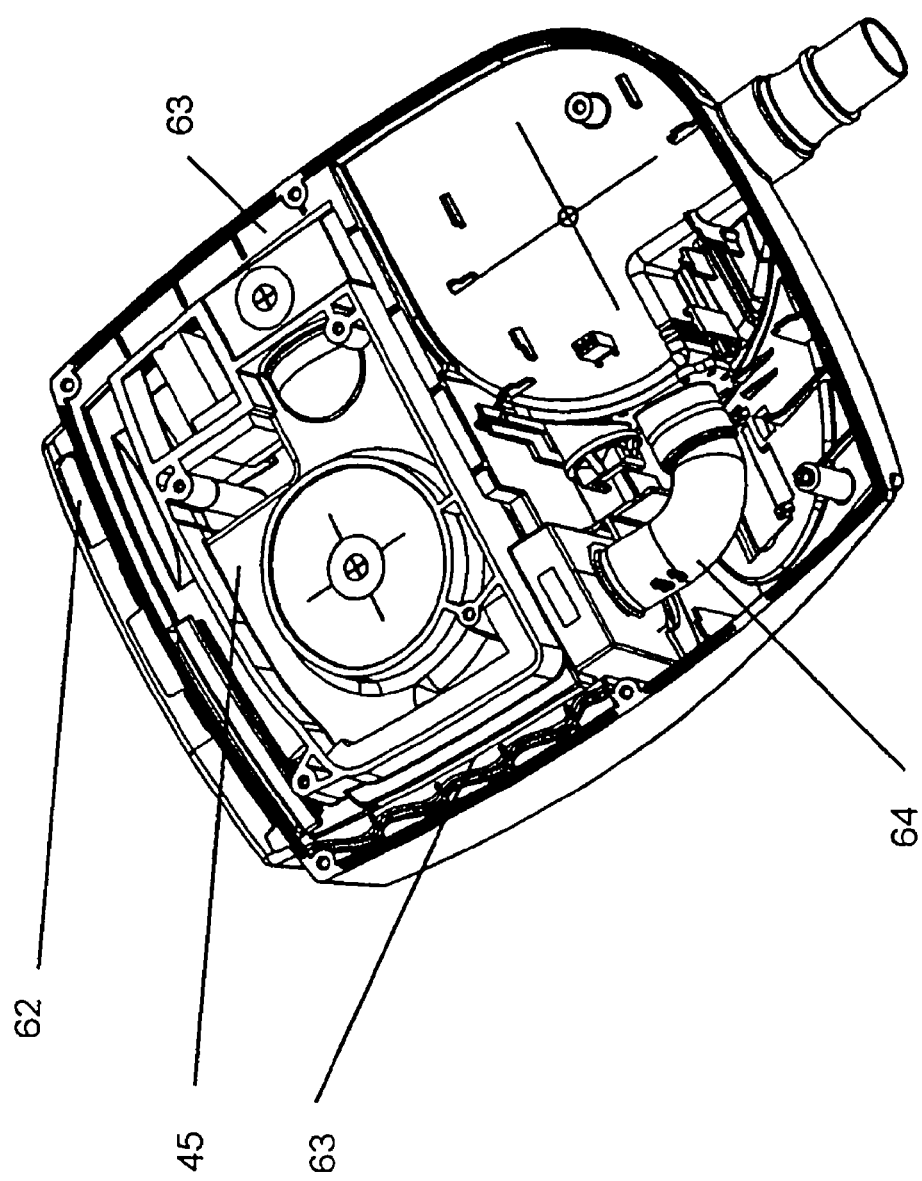
FIG. 14 is an illustration of an arrangement of a semi-enclosed sound-damping box in the ventilation device.
Figure 15:
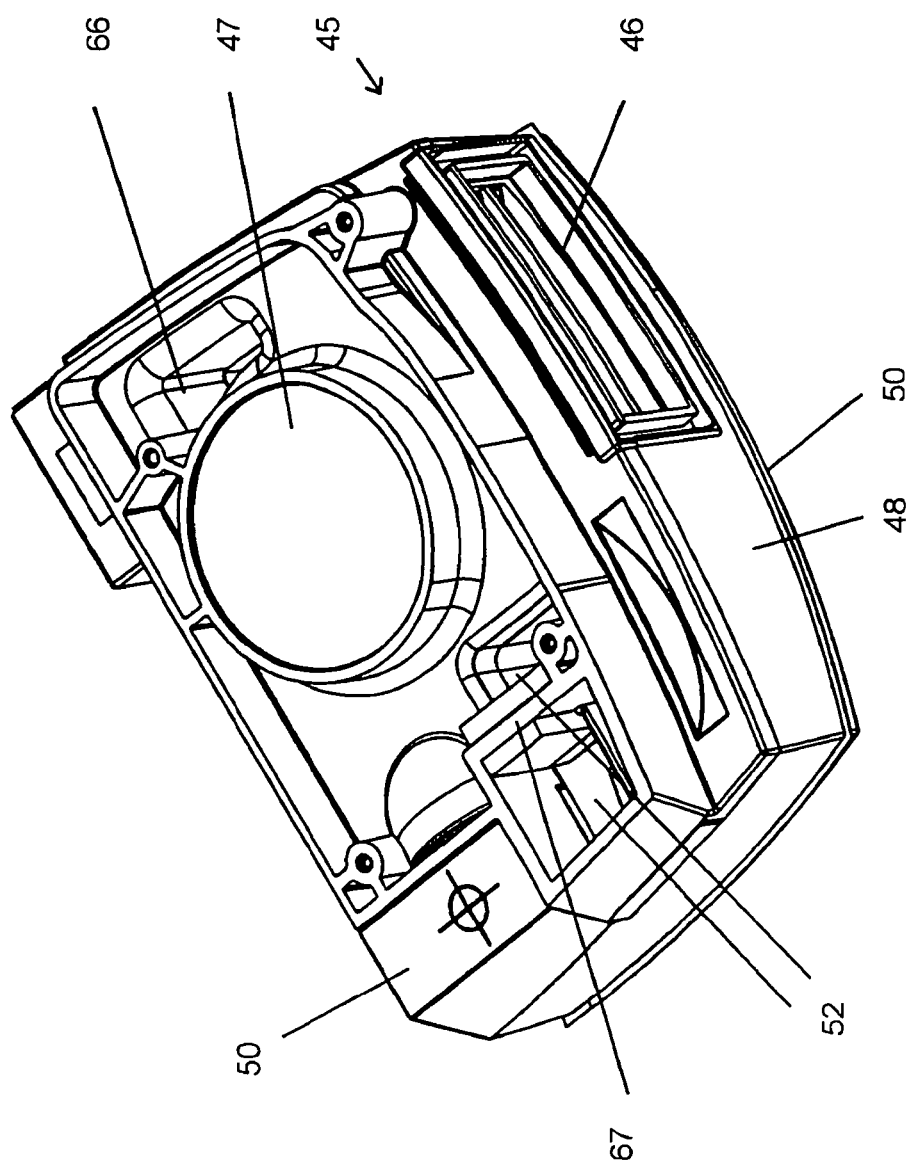
FIG. 15 is a perspective view of the device of FIG. 14.
Figure 16:
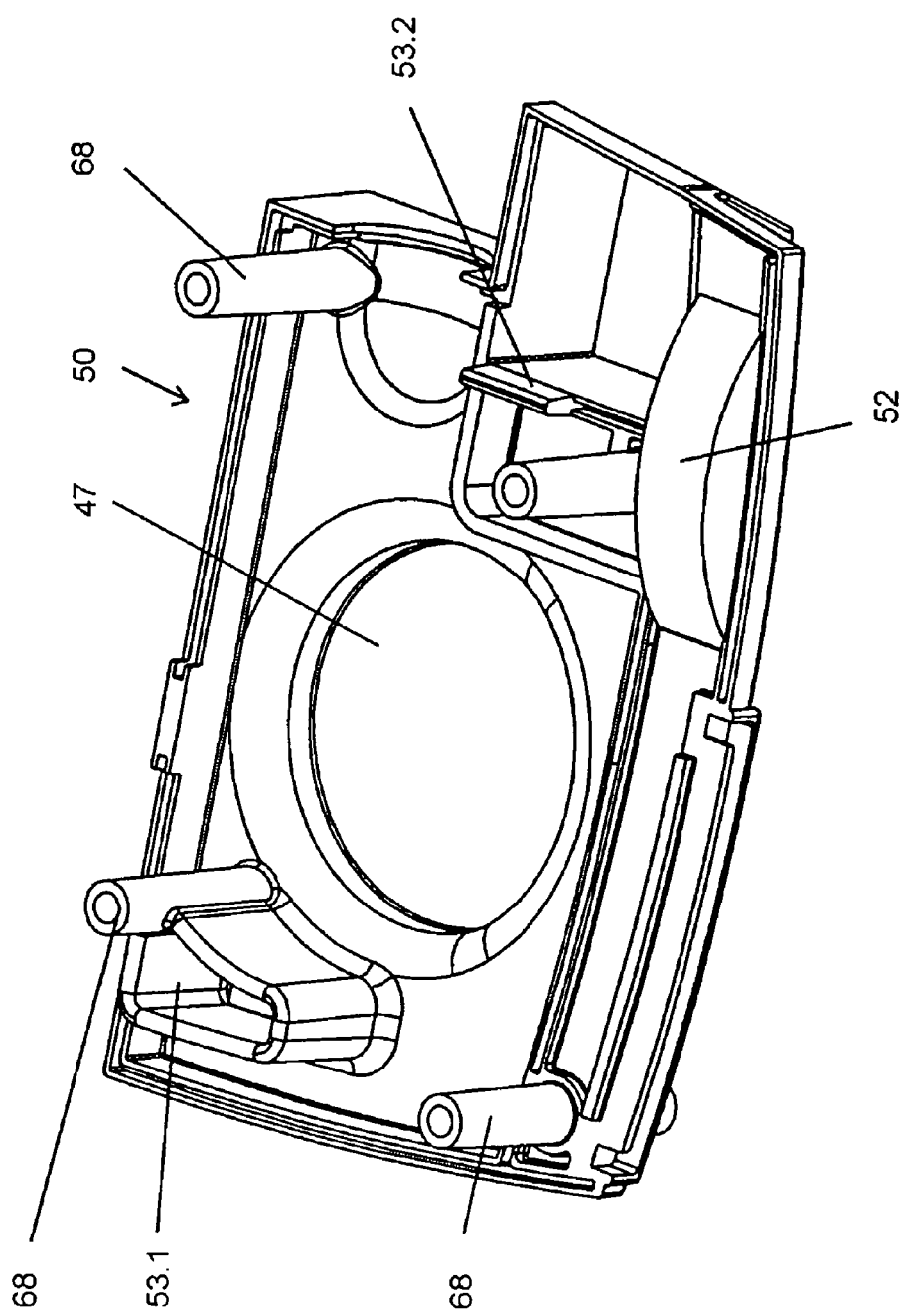
FIGS. 16, 17 and 18 are perspective views of the sound-damping box of the device.
Figure 17:
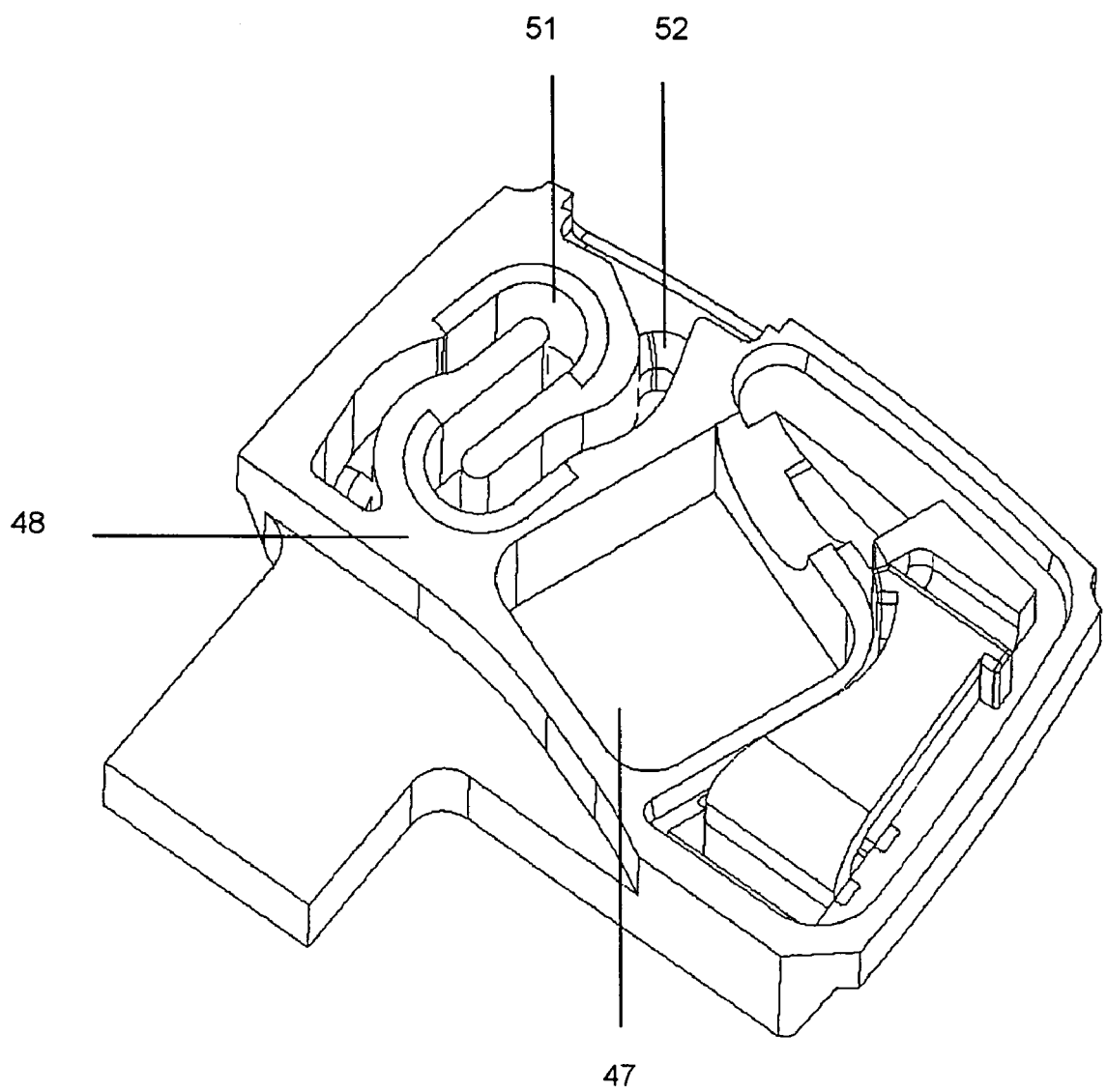
Figure 18:
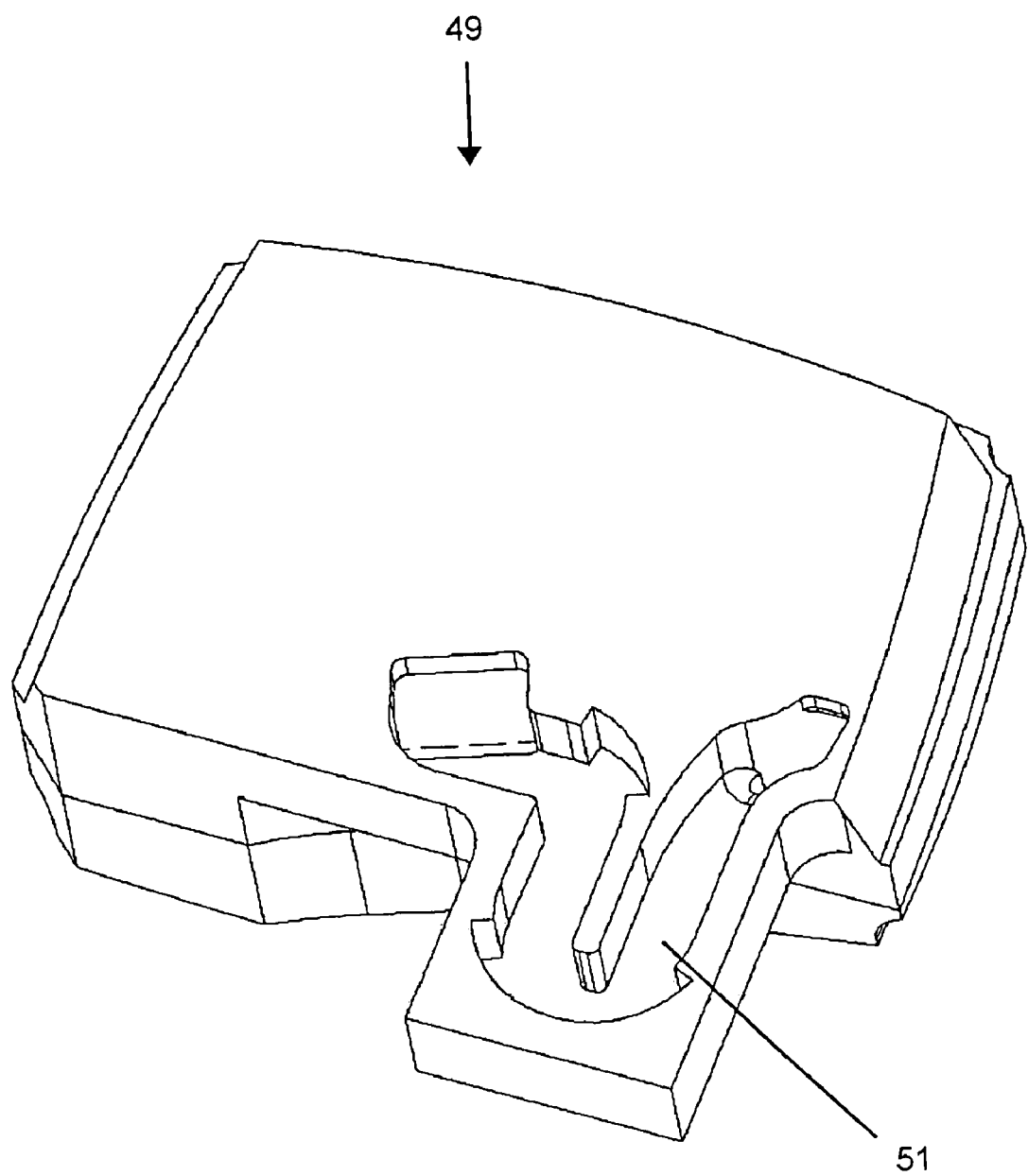

FIGS. 14 and 15 show the arrangement of the semi-enclosed sound-damping box (45) in the unit. In the assembled state, the top side of the sound-damping box (45) is provided with sealing material (63), which functions both as a support and as sound-damping material. The sound-damping box is preferably made of plastic and can be removed as a complete module from the unit. This makes cleaning easy. In the area of the sound-damping box (45), there is a receptacle (47) for the blower. The indrawn air passes through the air intake (46, 62), through a filter element (not shown), to the blower. In addition, a diversion (65) and a channels (66), which bridges the individual module, can be seen. The sound-damping material (67) is laid around a deflection.

FIG. 15 shows a rear view, in perspective, of the sound-damping box in the unit. The air intake (46) can be seen directly, because a cover cap (not shown) has been removed from the unit. In the installed state, the cover cap serves both as an appearance panel and as a sound-damping measure.

FIGS. 16 and 17, FIG. 18, FIG. 30, and FIG. 31 show the design of the sound-damping box (45), consisting of three modules. The bottom part (50), the middle part (48), and the top part (49) can be assembled to form the sound-damping box (45). The bottom part (50), the middle part (48), and the top part (49) define at least two essentially horizontal planes, in which the air is conducted and the sound is damped. Air-conducting areas (51) alternate with sound-damping areas (52), which can be designed as flat and/or expanded and/or foam-lined areas. At least two sound-damping principles are preferably implemented in the sound-damping box (45).

By means of at least one air-deflecting structure (53), the air is deflected at least once from a horizontal plane into a vertical plane and preferably again into a different horizontal plane. The air is preferably subjected to a two-fold change of planes.

For example, the air-conducting and sound-damping structures alternate at least once in the sound-damping box (45).

The flat, horizontal, sound-damping areas are located above or below the receptacle for the blower (47). So that the modules can be placed neatly on top of each other, guide posts (68) are integrated into the box, which also conceal the screw channels.

Figure 19:
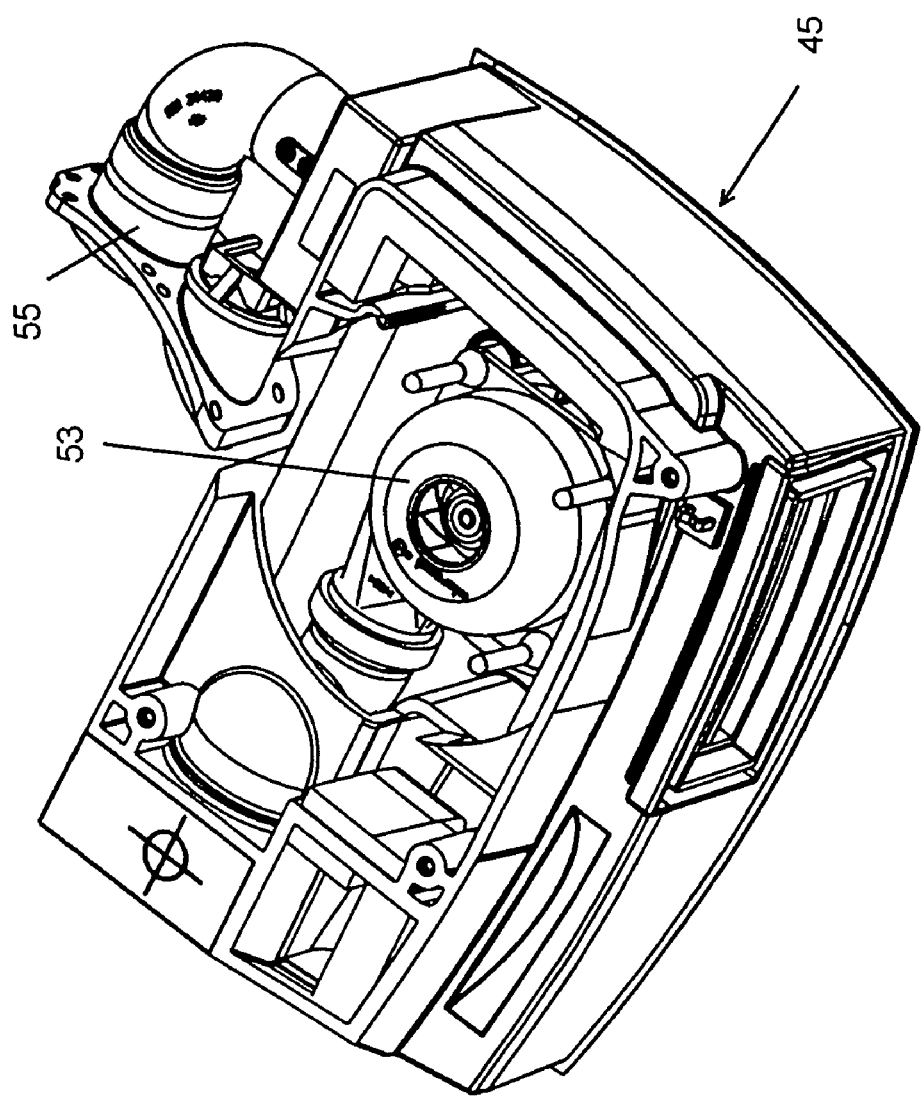
FIGS. 19 and 20 are additional views of the device.
Figure 20:
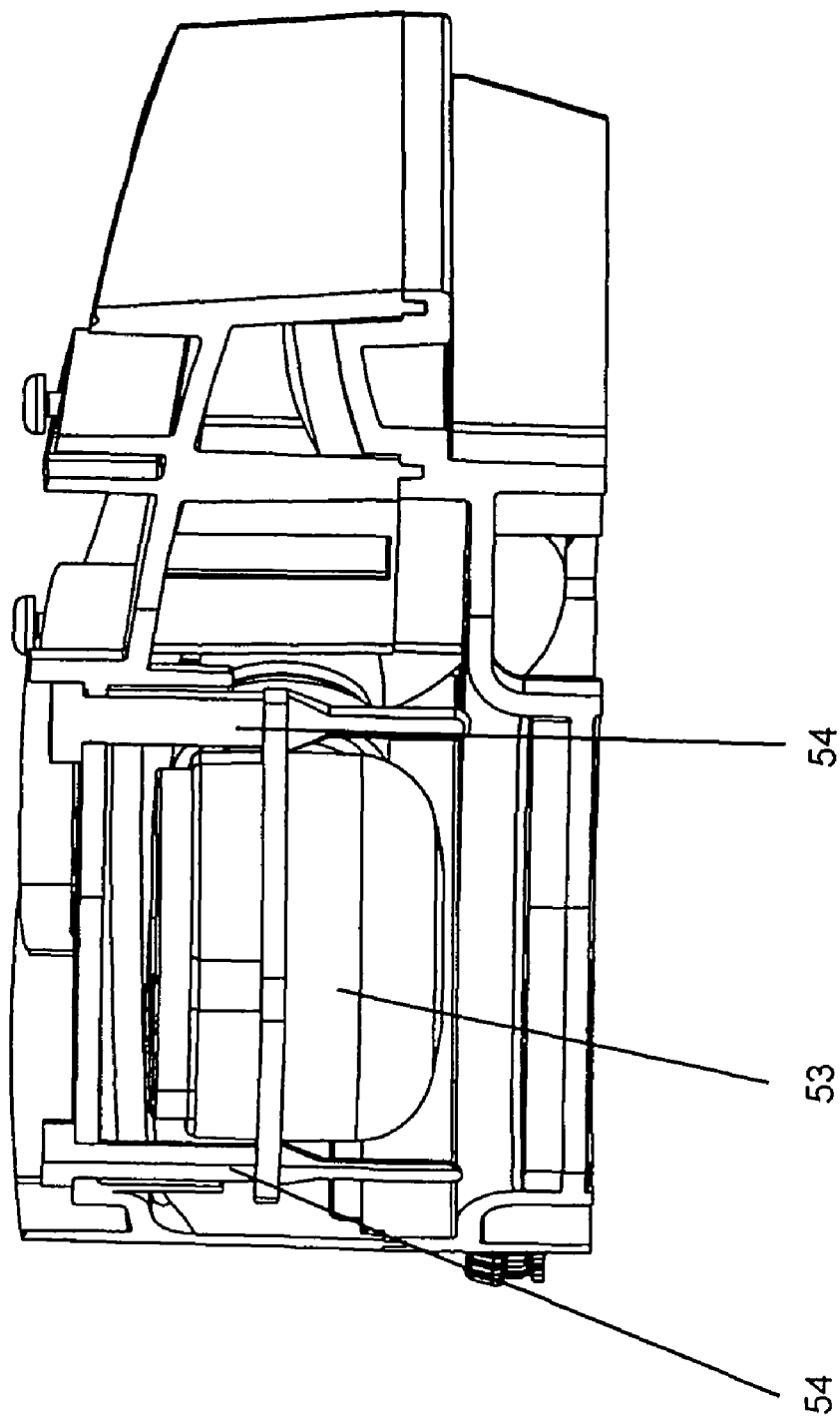

FIGS. 19 and 20 show additional views of the unit. The receptacle for the blower (53) inside the sound-damping box (45) is located essentially in the center, surrounded by air-conducting and sound-damping components. The blower (53) is located inside the sound-damping box (45) between the intake and delivery area (55) of the unit.

The blower is attached by soft, elastomeric elements (54), which preferably have both elastic and damping properties. The blower is attached from above. The blower is supported from above. Because of the way it is attached, the blower is suspended with freedom to move in 3 dimensions. At least two sound-damping structures are provided in the area of the blower.

The blower is mounted in the center of the unit, as far away as possible from the walls of the outer housing and/or surrounded by air-conducting components and/or surrounded by sound-conducting components.

Figure 21:
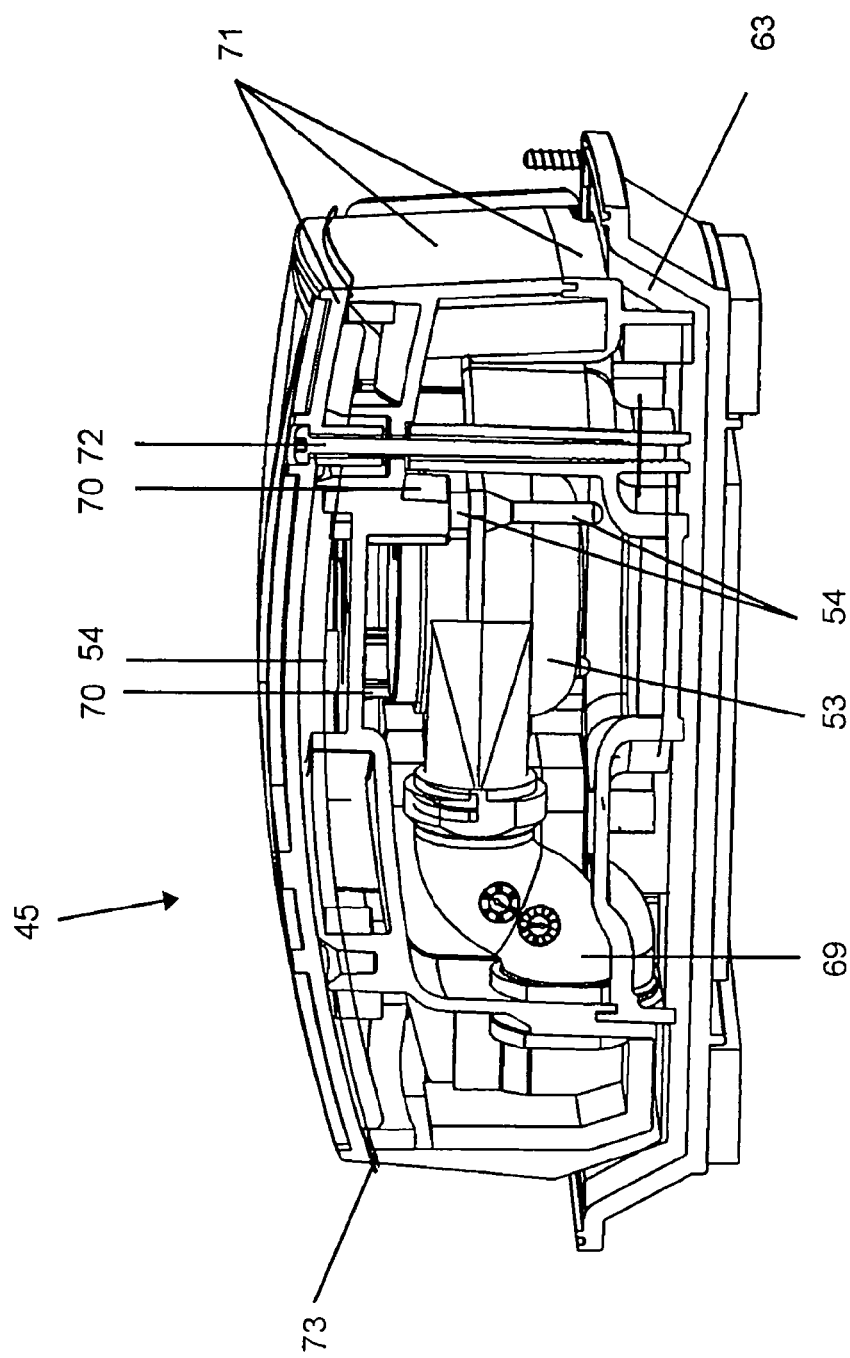
FIG. 21 is a cross sectional view of the sound-damping box.

FIG. 21 shows a cross section through the sound-damping box. The blower (53) is mounted on the elastomer hangers (54) and is also connected to the sound-damping box by an isolating hose (69). The sound-damping box (45) is built up out of three modules (71), which are connected by means of, for example, screwed joints (72). Clamped between the modules is sealing and damping material (73). This is also present underneath the box, as support material (63). The semi-cylindrical elements (70) attached to the blower suspension serve as deflection limiters.

Figure 22:
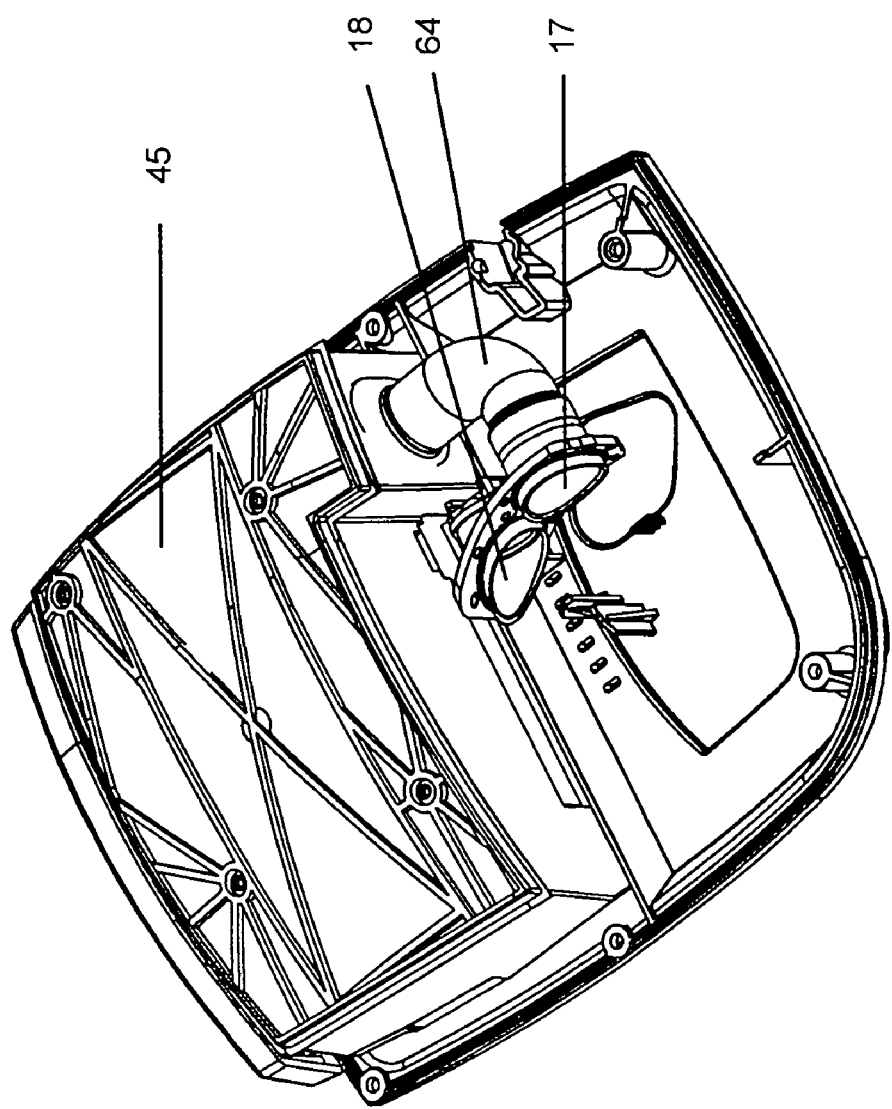
FIG. 22 is a perspective, partially broken view of the device with an isolating element embedded in the sound-damping box.

FIG. 22 shows the embedding of the sound-damping box (45), the air outlet (17), and the power supply (18) to the humidifier or dummy humidifier by way of an isolating element (64).

Figure 23:
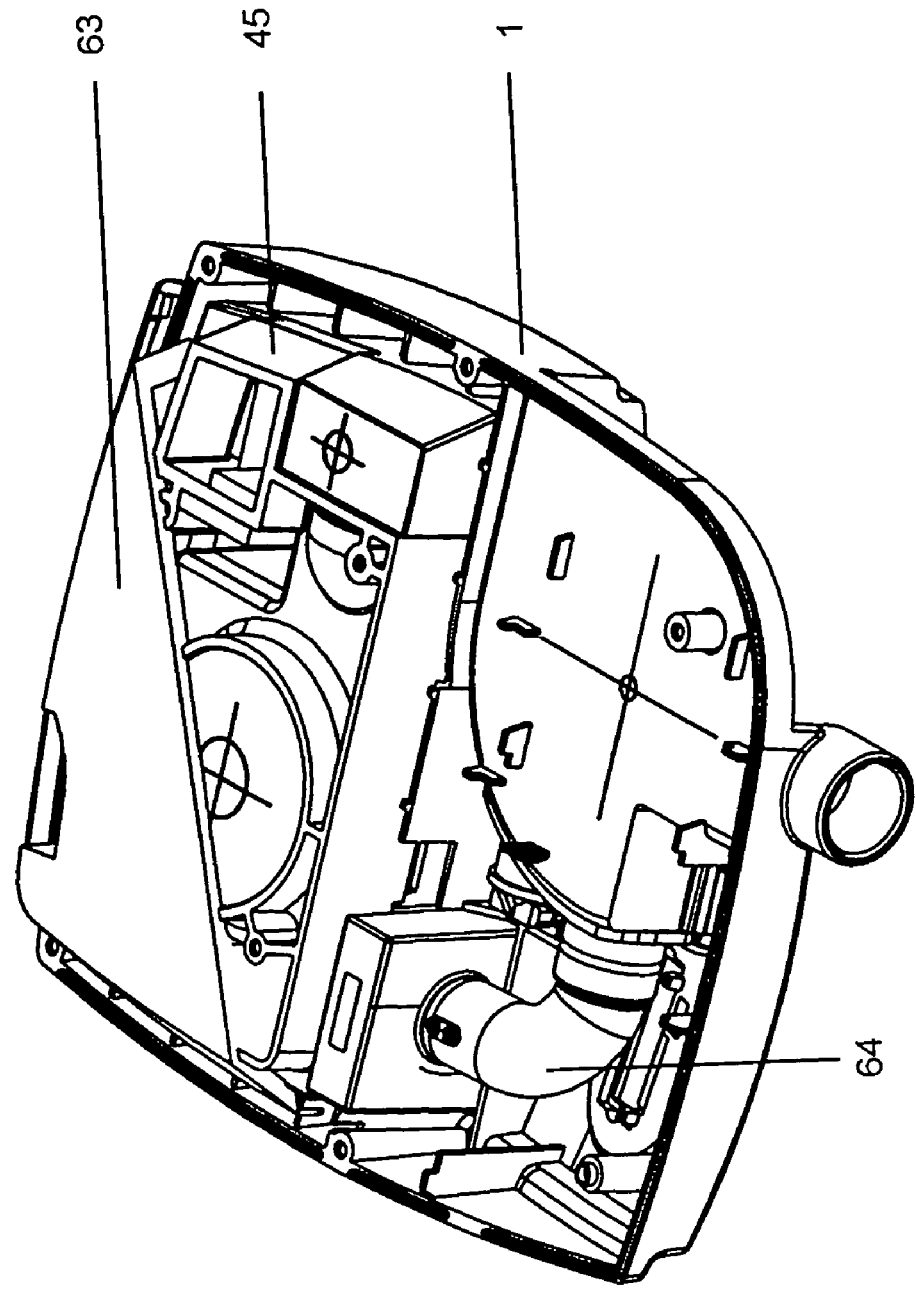
FIG. 23 is a partial perspective view of the ventilator with the semi-enclosed sound-damping box mounted in the ventilator enclosed by an damping/support/sealing material.

FIG. 23 shows the ventilator with the semi-enclosed sound-damping box (45) inside, which is closed by the damping/support/sealing material (63). The isolating element (64) has the job of isolating the semi-open sound-damping box (45) from the unit 1. Page 30, Lines 10-12. "The isolating element (64) has the job of isolating the semi-open sound-damping box (45) from the unit 1." should be changed to "The isolating element (64) has the job of isolating the semi-enclosed sound-damping box (45) from the unit 1."

To facilitate the installation of the damping material (63), the damping material is preferably provided with at least two openings, and the associated surfaces of the top part of the unit are provided with markings in the area which will face the damping material (63). FIG. 23 shows two cross-shaped markings, arranged essentially diagonally from each other, the center of each cross being surrounded by a circle. The openings in the area of the damping material (63) can be preferably circular. During installation, it is necessary only to be sure that the centers of the openings line up with the centers of the cross-like markings. Once this is done, an optimal installation state is guaranteed. As a rule, two openings and two assigned cross-shaped markings will prove sufficient as a means of simplifying the installation process.

Figure 24:
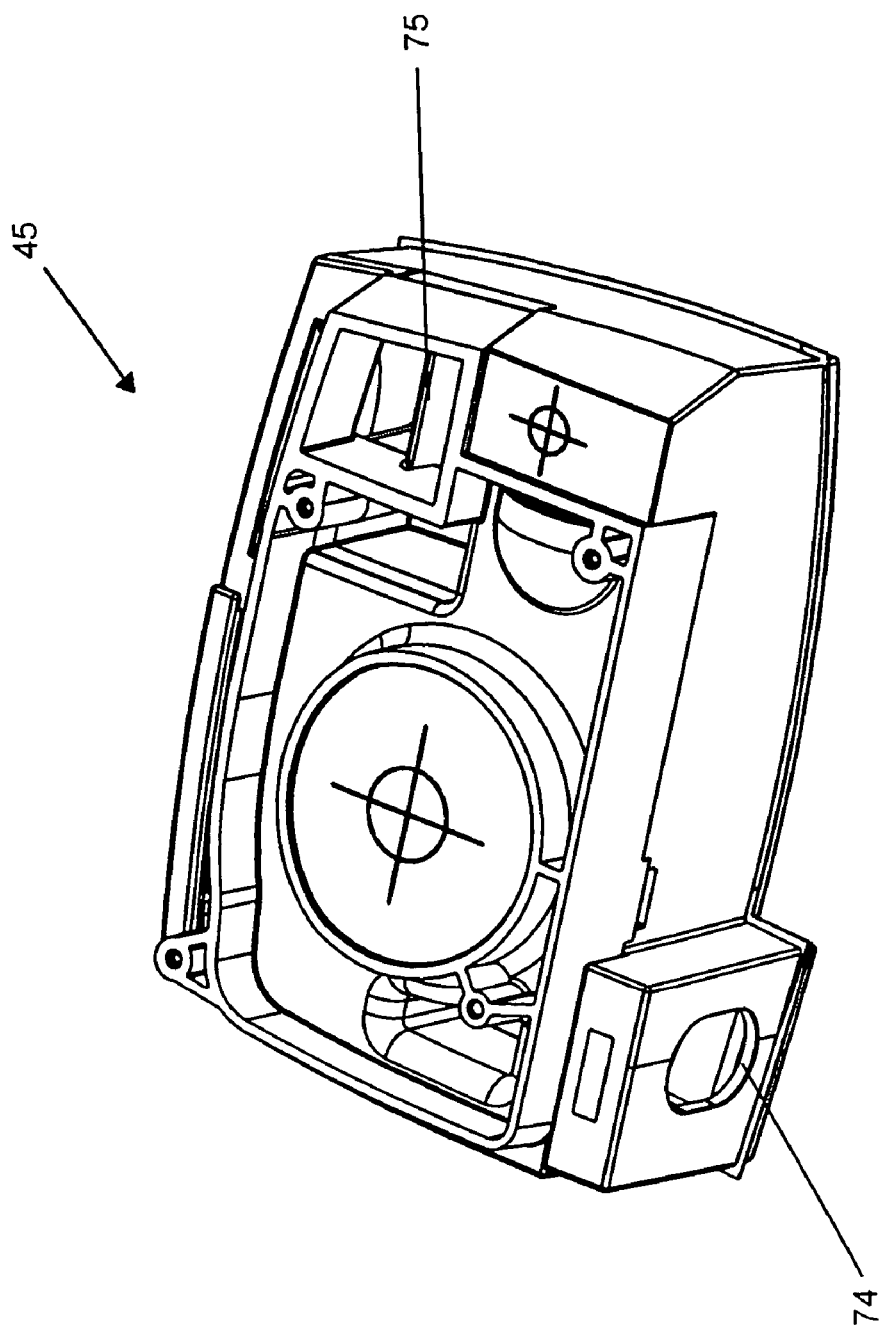
FIG. 24 is a perspective view showing the sound-damping box with a mating profile for an isolating element.

FIG. 24 shows a view of the sound-damping box (45) with a mating profile (74) for an isolating element (not shown).

Figure 25:
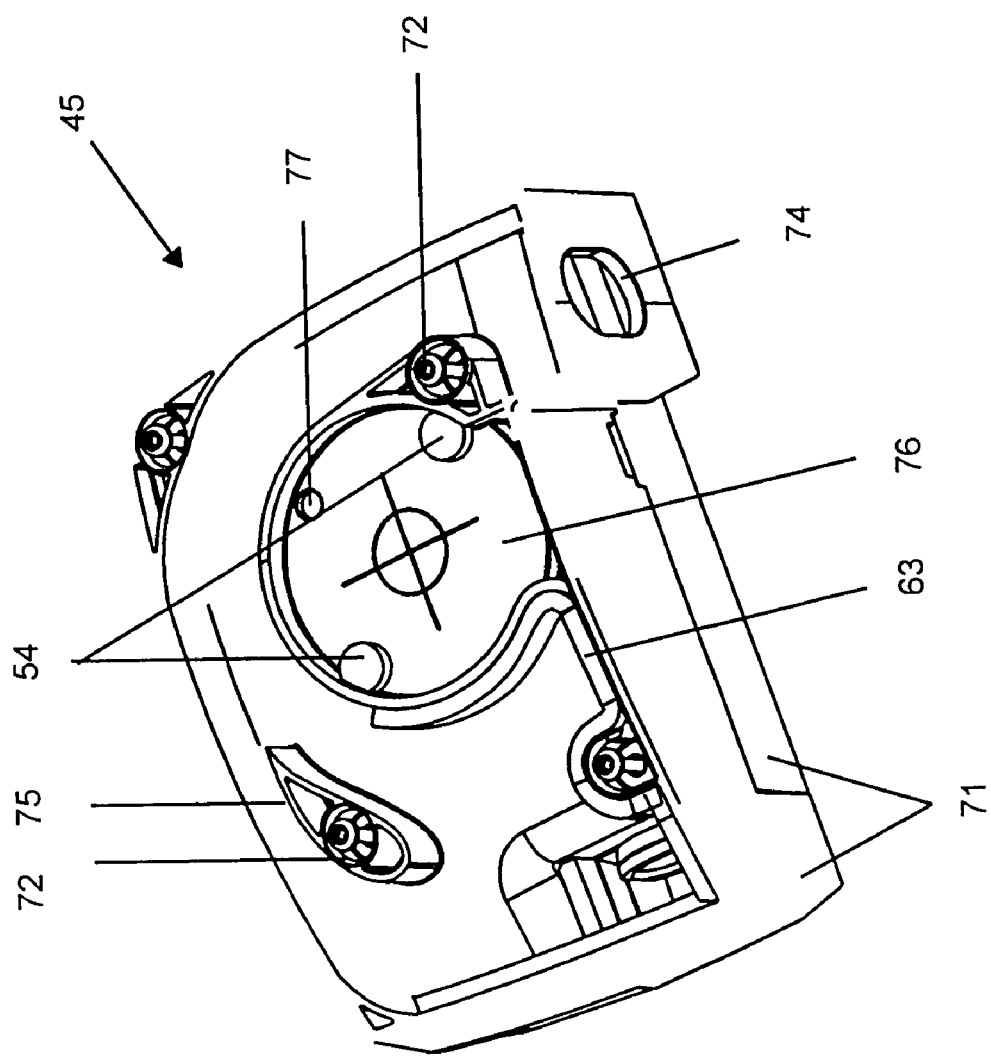
FIG. 25 is a perspective view of the sound-damping box with modules for suspending the blower.

FIG. 25 shows a view of the sound-damping box (45), which has modules (71), a mating profile (74) for an isolating hose (not shown), screw joints (72), and bores (77) for the hangers (54) used to suspend the blower. It is easy to see how the existing geometries, here the positioning (76) of the blower and a screw joint (72), can be used with the help of sound-damping material (63), for example, to form the various planes and structures of the air guides and sound-damping areas. The blower hangers (54) also simultaneously close off the bores (77) and thus also the two planes separated by the module (71).

Figure 26:
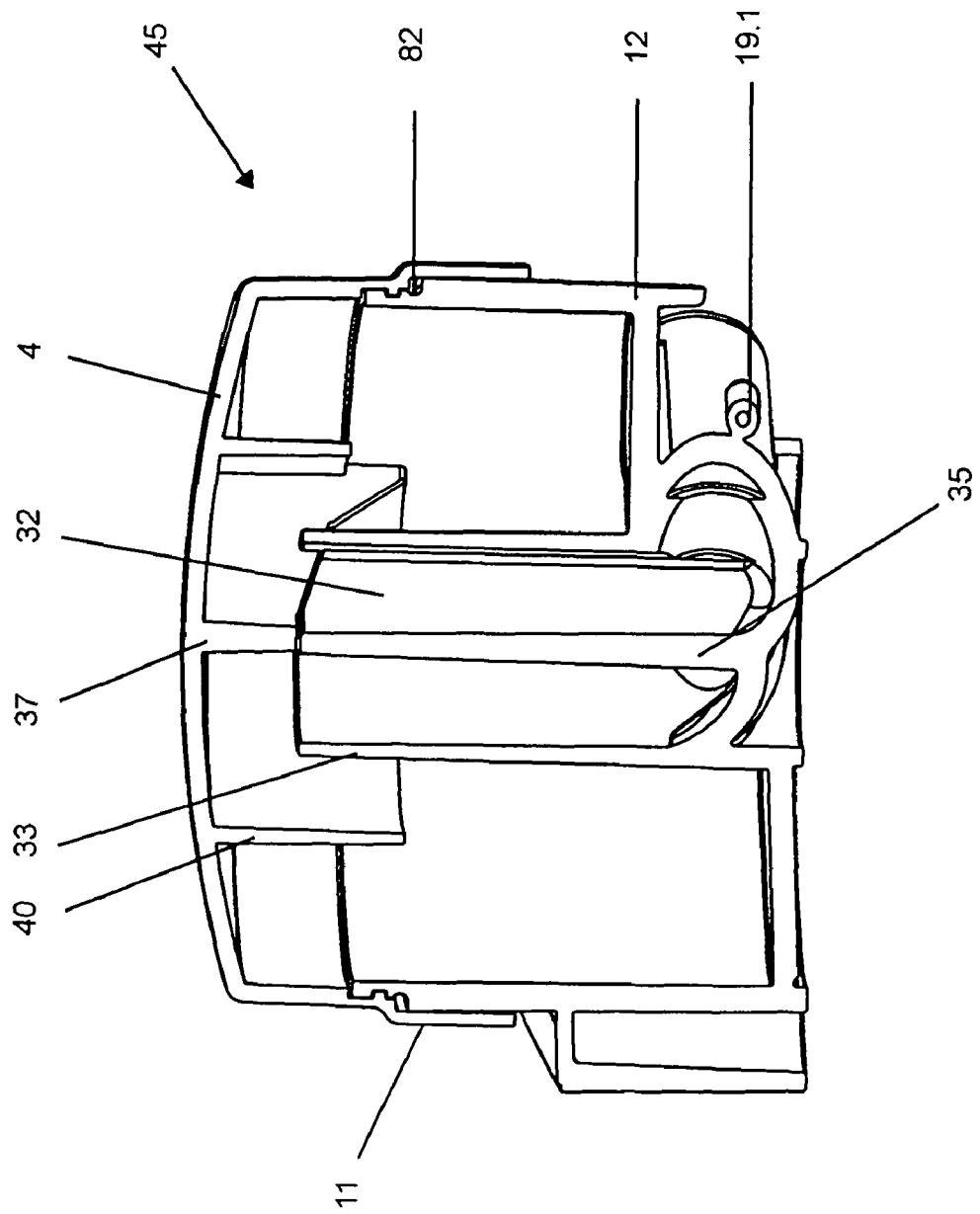
FIG. 26 is a cross sectional view of another breathing air humidifier.

FIG. 26 shows a cross section through a breathing air humidifier (9) with a top part (11) and a bottom part (12). Between them, a seal (82) is inserted, which consists preferably of an O-ring. A separating plane (35) on the bottom part (12) and a separating plane (37) on the top part can also be seen between the vertical inlet and outlet channels. The air inlet (33) and the air outlet (32) are completed by a collar (40), which influences the flow of air in the desired manner. The pressure measurement connection (19.1) can also be seen.

Figure 27:
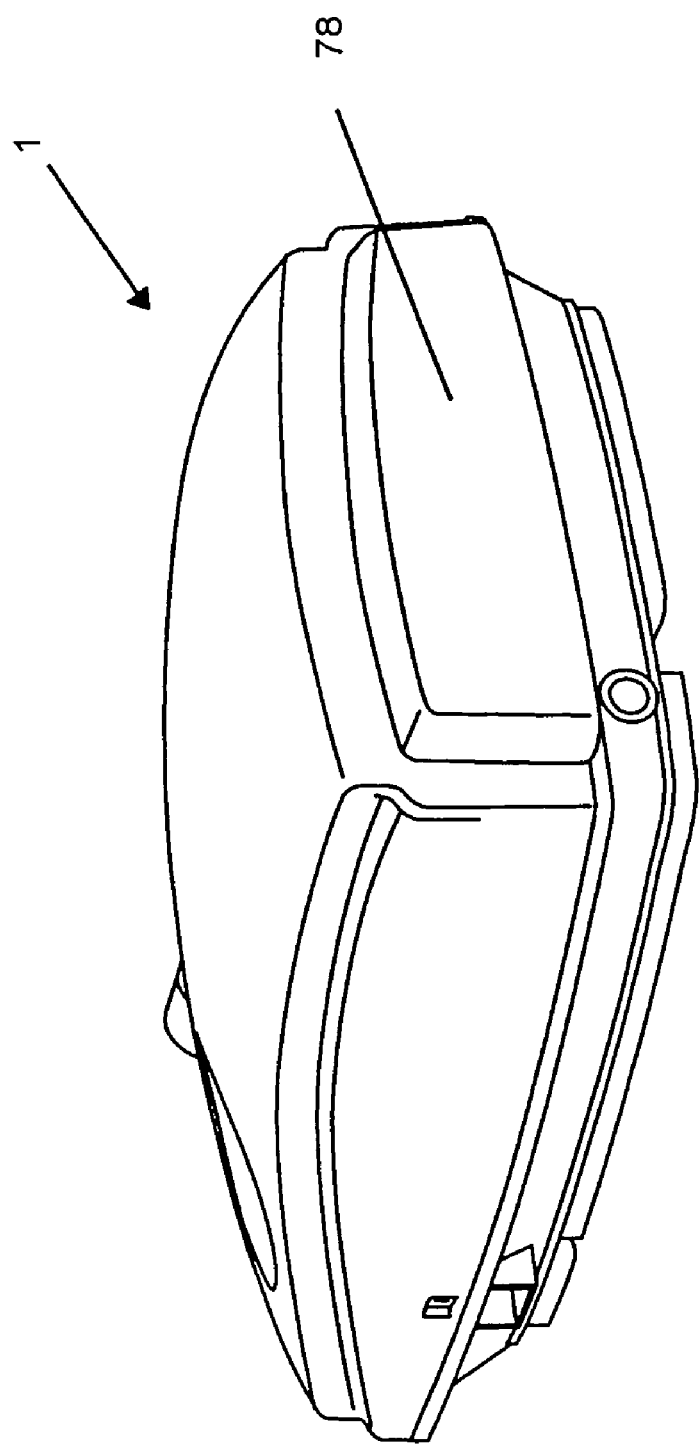
FIG. 27 is a perspective rear view of the device with an air intake cover cap.

FIG. 27 shows a rear view of the unit (1) and an air intake cover cap (78) for the air intake into the unit, which contributes to the damping of the intake sound.

Figure 28:
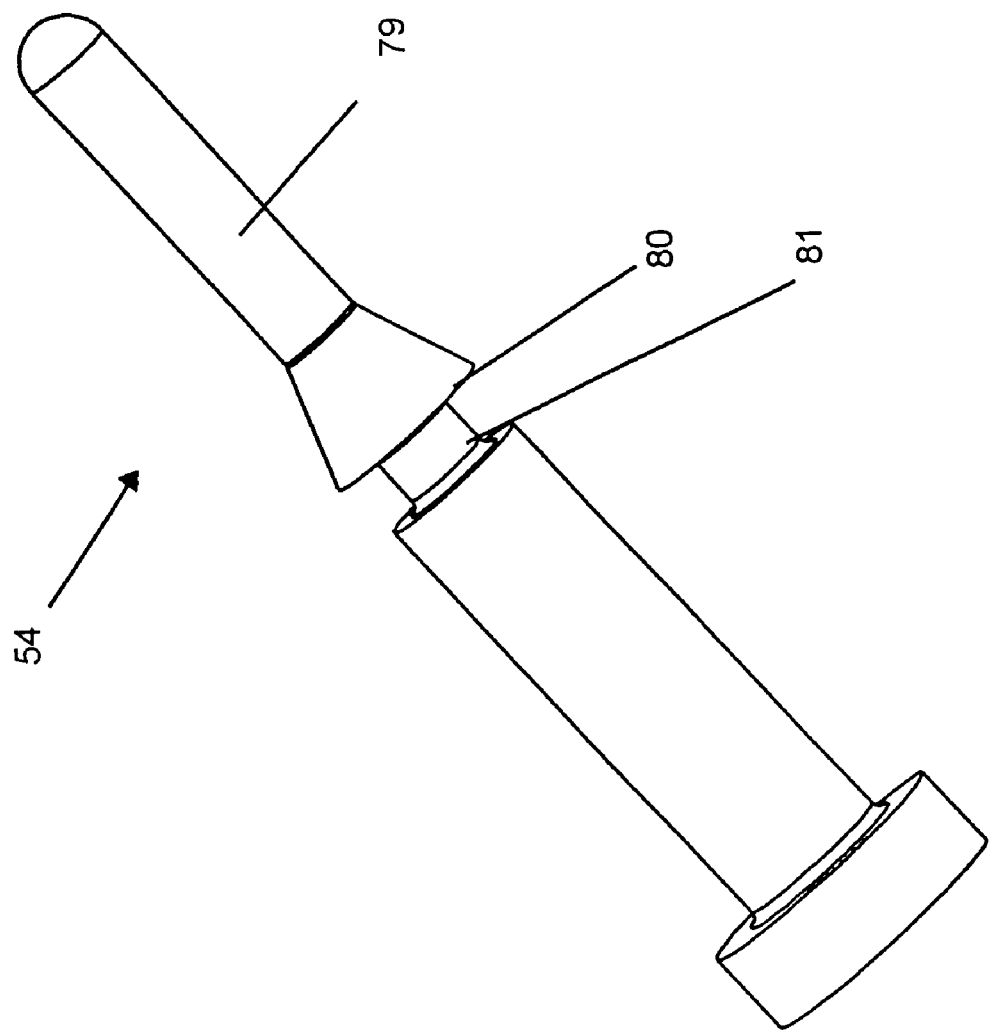
FIG. 28 is a perspective view of a blower hanger.

FIG. 28 shows the design of a blower hanger (54), which is provided with a guide tip (79), a shoulder (80), and a circumferential groove (81) for rapid installation of the blower.

Figure 29:
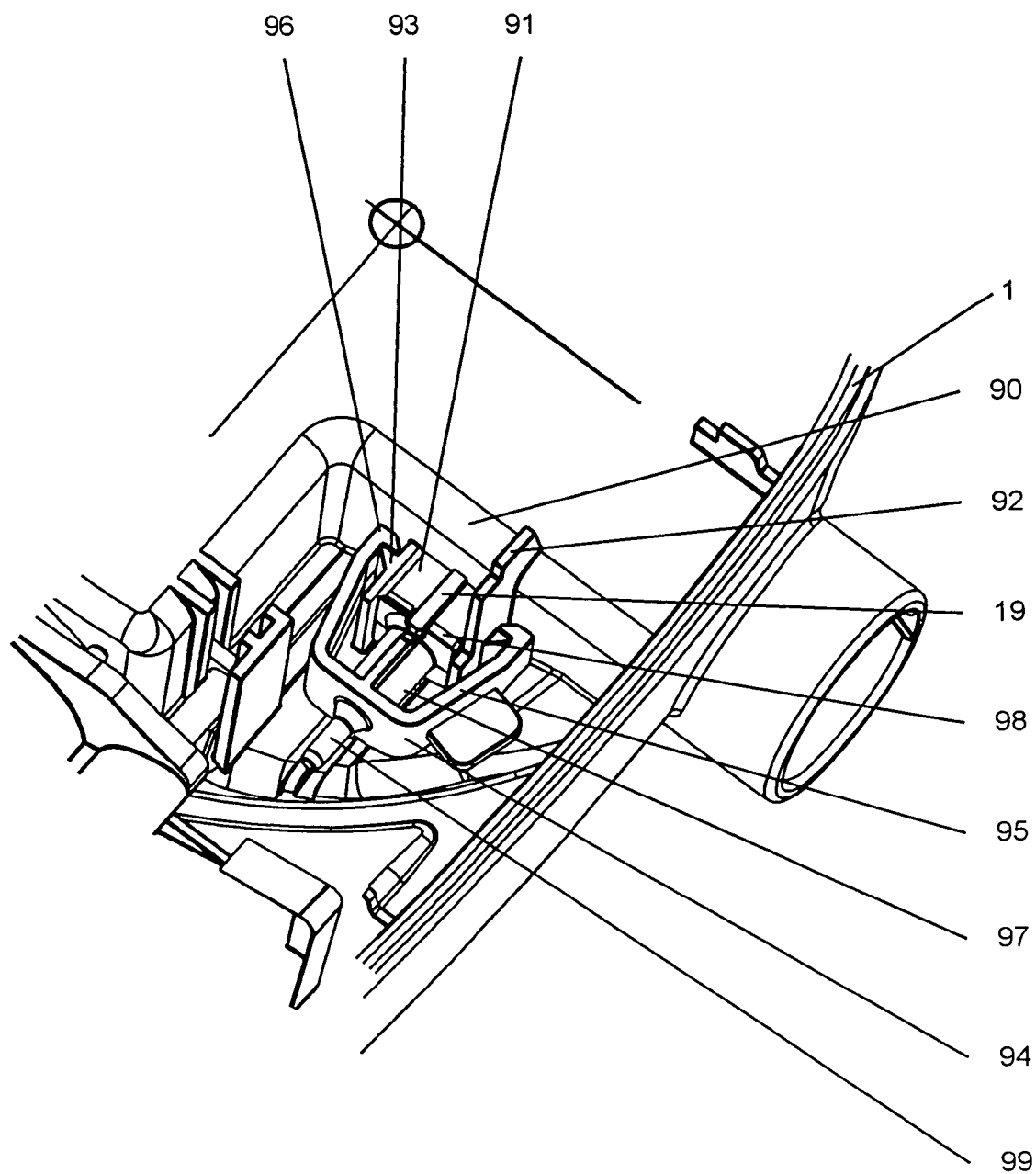
FIG. 29 is a perspective view of a detail of the interior space of the device.
Figure 30:
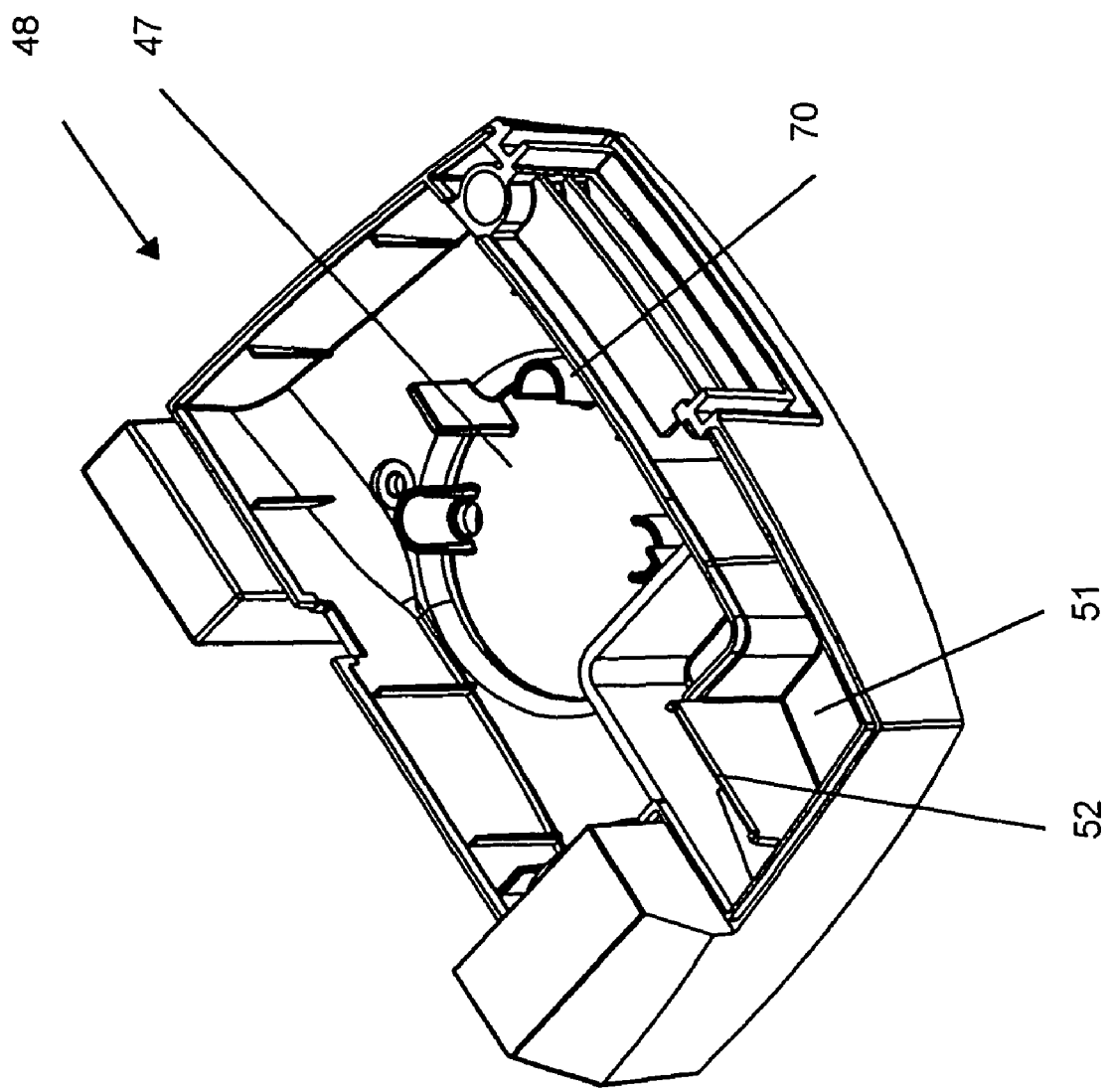
FIGS. 30 and 31 are perspective views of the sound-damping box of the device.
Figure 31:
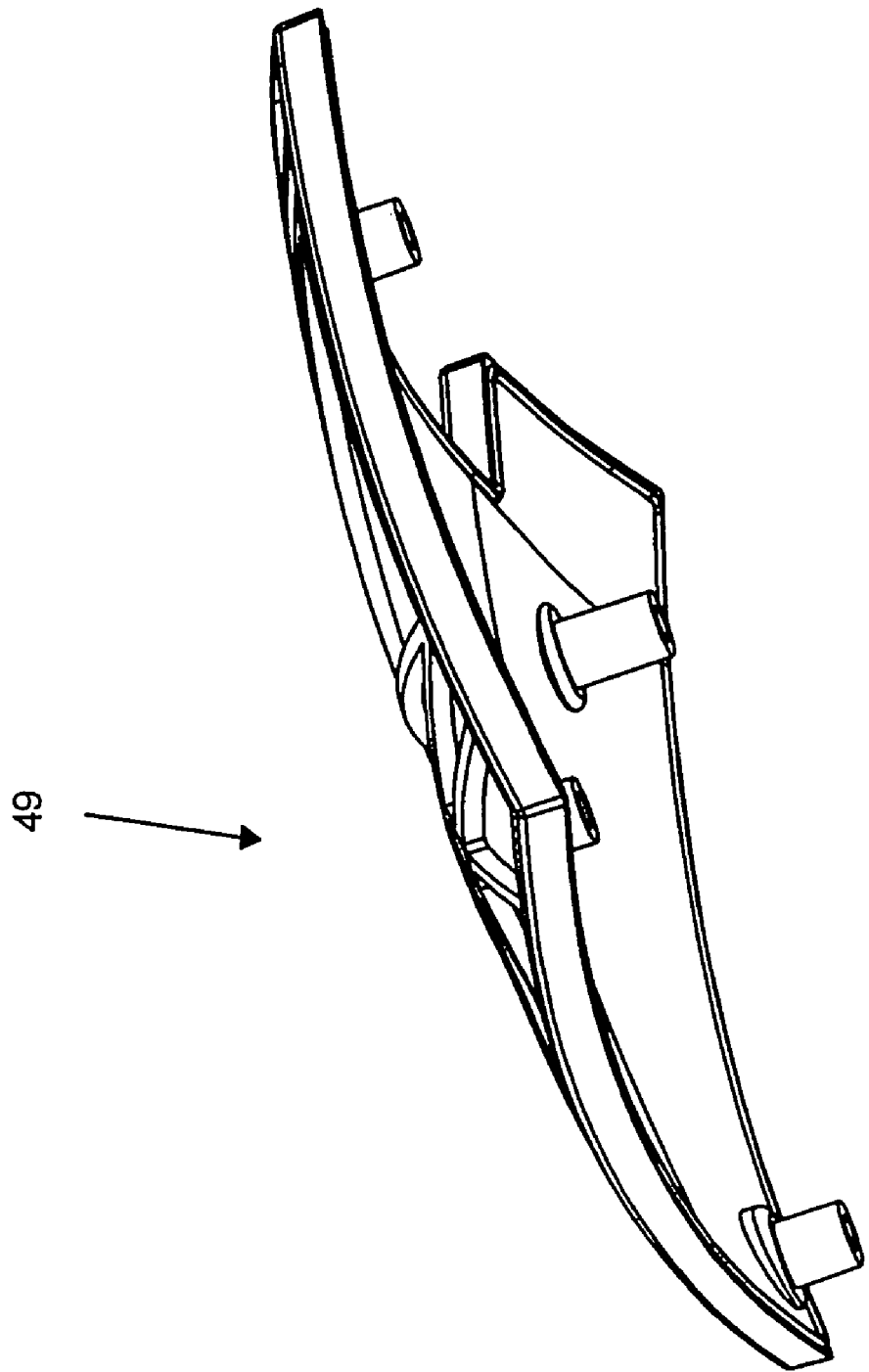

FIG. 29 shows another partial view of an interior space of the unit (1). In particular, the figure shows how the internal connections to the pressure-measurement connection are realized. The pressure-measurement connection (19) comprises, first, an opening (not visible in FIG. 29) in an interior wall (90) of the equipment housing, into which a sealing element (91) of a preferably elastomeric material is inserted. The sealing element (91) is held in place by lateral webs (92, 93). The connecting piece on the breathing air humidifier can be introduced into the sealing element (91) from the outside.

The lateral webs (92, 93) have, on the outside, a latching profile, which can be gripped from behind by an adapter (94). The adapter (94) has mounting sidepieces (95, 96), which engage in the retaining profile. The sidepieces are carried by a central element (97) of the adapter (94). One end of the central element can be plugged into the sealing element (91). A stop plate (98) is provided to ensure that the adapter (94) is positioned precisely.

A connector (99) of the adapter (94) facing away from the sealing element (91) is used to accept a pressure-measuring hose (not shown), which establishes a connection with the pressure sensor itself. In particular, the pressure sensor is to be located in the area of the control circuit board of the unit.

While specific embodiments of the invention have been shown and described in detail to illustrate the inventive principles, it will be understood that the invention may be embodied otherwise without departing from such principles.

We claim:

1. A ventilator with integratable breathing air humidifier, comprising at least two defined air pathways provided in a region of the breathing air humidifier, and a sound-damping box, and combined with a breathing air humidifier or a dummy element, wherein the dummy element has sound-damping properties.

2. The ventilator with integratable breathing air humidifier according to claim 1, wherein the breathing air humidifier can be installed and fixed on a horizontal surface of the ventilator.

3. The ventilator with integratable breathing air humidifier according to claim 1, comprising a breathing air humidifier having at least a top part and a bottom part, and a water reservoir provided in the bottom part, wherein the top part cannot be removed from the bottom part when the unit is in at least one operating mode.

4. The ventilator with breathing air humidifier according to claim 1, at least one water reservoir, and at least one filling device for the water reservoir in the breathing air humidifier, wherein the filling device can be operated with one hand and/or opened with one hand.

5. The ventilator according to claim 1, wherein the air is diverted in the horizontal and/or vertical direction at least twice by more than 80°±10° inside the sound-damping box.

6. The ventilator with a breathing air humidifier according to claim 1, and further compromising at least one connecting element for connecting to a breathing hose, wherein the connecting element holds the breathing air humidifier in place on the ventilator.

7. The ventilator according to claim 1, wherein the sound-damping box comprises at least two modules.

8. The ventilator according to claim 7, wherein the modules have openings which define air-conducting and/or sound-damping areas.

9. The ventilator according to claim 1, wherein the sound-damping box is made essentially of plastic material.

10. The ventilator according to claim 1, wherein indrawn air is diverted at least once from the horizontal to the vertical direction or at least once from the vertical direction, to the horizontal direction in the sound-damping box.

11. The ventilator according to claim 1, wherein at least two sound-damping principles are realized in the ventilator.

12. The ventilator according to claim 1, wherein at least one blower is mounted in the ventilator by means of elastomeric elements.

13. The ventilator according to claim 1, wherein at least one blower is fastened in place in the ventilator by suspension from above.

14. The ventilator with an air humidifier according to claim 1, wherein, in the housing of the ventilator, a receptacle is provided into which at least part of the air humidifier is inserted, and which has at least one connecting element for the functional connection of the air humidifier to the ventilator.

15. The ventilator according to claim 1, with a receptacle to receive a breathing air humidifier, wherein, in the area of the opening, a dummy element is provided, which, in the area of the receptacle, has a connecting channel for connecting a breathing gas intake line to a breathing gas discharge line, and wherein a surface contour of the dummy element merges continuously with the surface contour of a housing of the ventilator.

16. The ventilator according to claim 1, comprising a receptacle for either a breathing air humidifier or a dummy element, characterized in that both the dummy element and the breathing air humidifier have a configuration which allows them to be connected to a locking element, which holds the module-like dummy element or breathing air humidifier in place in the area of the receptacle and which is designed for single-handed operation.

17. The ventilator according to claim 1, comprising a blower installed in a sound-damping box positioned inside a housing of the ventilator and supported elastically with respect to the ventilator housing, wherein the sound-damping box is semi-enclosed.

18. The ventilator with a sound-damping box positioned inside a ventilator housing according to claim 17, wherein the sound-damping box is semi-enclosed, and open areas of the sound-damping box can be closed off by sound-damping material.

19. The sound-damping box according to claim 18 which is closed off in the delivery area and open in the intake area, and in which a sealing action is created in the intake area in combination with the overall design, whereas the box is leak-tight in itself in the delivery area.

20. The sound-damping box according to claim 19 which is completely closed in the area of high or positive pressures, wherein, in the intake area, a combination with at least one other structural element is required to provide a closed structure and flow guidance.

21. The ventilator according to claim 1 with a breathing gas blower, which is supported elastically, wherein the elastic support is comprised of at least one pin made of elastomeric material, which has a retaining profile, into which a mating profile of the blower engages.

22. The ventilator with a breathing air humidifier according to claim 1, wherein the ventilator has a pressure-measuring connection located downstream of the humidifier.

23. The ventilator according to claim 1, comprising a dummy element for replacing a breathing air humidifier, wherein the ventilator has a pressure measurement connection located in the outlet area of the dummy element.

24. The ventilator according to claim 1, comprising a breathing air humidifier which consists of a bottom part and a top part, wherein the top part has an external contour such that, after the top part and the bottom part have been assembled and installed so that the ventilator is operational, the components cannot be separated from each other.

25. The ventilator according to claim 1, combined with either a breathing air humidifier or a dummy element, further comprising a pressure sensor mounted on a control circuit board of the ventilator and connected to a measurement site through a pressure measurement line.

26. The ventilator according to claim 1 with an air intake, wherein the air intake being located in a rear area of the unit and provided with a cover cap, configured to serve both as an appearance panel and as a sound-damping element.

27. The ventilator according to claim 1 with an interior space enclosed by an equipment housing, wherein at least one structural element is mounted on a sound-damping support, wherein the sound-damping support has at least one opening, and wherein at least one marking corresponding to the opening is provided on the mounting surface provided for the sound-damping element.

28. The ventilator according to claim 1 having at least two vertical planes, where at least one of the planes is subjected to gas of a higher pressure.

29. The humidifier according to claim 14 with vertical, flow-carrying elements, which are located in the center of the humidifying chamber to prevent or to reduce the intrusion of water into the unit and/or into the patient hose in the event that the unit tips.

30. The ventilator according to claim 1 with humidifier, wherein the humidifier is held in place by means of at least one connecting element in the area of the ventilator and in that the connecting element also serves to attach the hose.

31. The ventilator according to claim 1 in which a ventilating hose is connected to the ventilator by means of at least one connecting element, wherein the connecting element (4) has a hose area (24), which is connected to the hose (5), and a unit area, which is connected to the ventilator.

32. The ventilator according to claim 1 having an opening for a connecting element for rapid, one-handed connection of a ventilator hose to the ventilator by means of the connecting element, wherein the connecting element (4) has a hose area (24), which is connected to the hose (5), where, via the actuation of an operating element (13), a functional part (30) of the connecting element is locked and/or unlocked in an opening in the ventilator, and thus the connecting element (4), with hose connected, is attached and detached from the ventilator.

* * * * *